United States Patent
Linderman et al.

(10) Patent No.: US 10,631,973 B2
(45) Date of Patent: Apr. 28, 2020

(54) COMPOSTIONS AND METHODS FOR TISSUE REPAIR

(71) Applicants: Stephen Linderman, St. Louis, MO (US); Guy Genin, St. Louis, MO (US); Stavros Thomopoulos, Clayton, MO (US); Kollbe Ahn, Santa Barbara, CA (US); Victor Mark Birman, Chesterfield, MO (US)

(72) Inventors: Stephen Linderman, St. Louis, MO (US); Guy Genin, St. Louis, MO (US); Stavros Thomopoulos, Clayton, MO (US); Kollbe Ahn, Santa Barbara, CA (US); Victor Mark Birman, Chesterfield, MO (US)

(73) Assignee: Washington University, St. Louis, MO (US)

( * ) Notice: Subject to any disclaimer, the term of this patent is extended or adjusted under 35 U.S.C. 154(b) by 107 days.

(21) Appl. No.: 15/455,792

(22) Filed: Mar. 10, 2017

(65) Prior Publication Data
US 2017/0360554 A1   Dec. 21, 2017

Related U.S. Application Data

(63) Continuation-in-part of application No. 14/940,541, filed on Nov. 13, 2015, now Pat. No. 10,314,574.
(Continued)

(51) Int. Cl.
*A61F 2/08*   (2006.01)
*A61L 17/14*   (2006.01)
(Continued)

(52) U.S. Cl.
CPC .......... *A61F 2/08* (2013.01); *A61B 17/06166* (2013.01); *A61L 17/145* (2013.01); *A61L 24/0005* (2013.01); *A61L 24/0015* (2013.01); *A61L 24/0031* (2013.01); *A61B 17/1146* (2013.01); *A61B 2017/00884* (2013.01); *A61B 2017/00951* (2013.01); *A61F 2/28* (2013.01); *A61F 2220/005* (2013.01);
(Continued)

(58) Field of Classification Search
CPC .......... A61B 17/06166; A61B 17/1146; A61B 2017/00951; A61B 17/06; A61B 2017/00893; A61B 17/00491; A61B 17/04; A61B 2017/00884; A61B 2017/06185; A61L 17/145
USPC ........................................................ 606/228
See application file for complete search history.

(56) References Cited

U.S. PATENT DOCUMENTS 6,264,675 B1   7/2001   Brotz
8,142,475 B2   3/2012   Viola
(Continued)

OTHER PUBLICATIONS

Ahn et al. (2015)—High-performance mussel-inspired adhesives of reduced complexity, Nature Communications, 6, pp. 1-7.
(Continued)

*Primary Examiner* — George J Ulsh

(57) ABSTRACT

Provided herein are compositions and methods for treating a subject with damaged tissue, such as an injury associated with a tissue to tissue (e.g., a connective tissue-to-connective tissue or tissue to bone) interface. One aspect provides an adhesive film or adhesive layer, optionally comprising a biomaterial, tissue growth factors, including CTGF/CCN2, or cells.

26 Claims, 21 Drawing Sheets

Related U.S. Application Data

(60) Provisional application No. 62/309,214, filed on Mar. 16, 2016, provisional application No. 62/079,965, filed on Nov. 14, 2014.

(51) Int. Cl.

| | | |
|---|---|---|
| *A61L 24/00* | (2006.01) | |
| *A61B 17/06* | (2006.01) | |
| *A61F 2/28* | (2006.01) | |
| *A61B 17/00* | (2006.01) | |
| *A61B 17/11* | (2006.01) | |

(52) U.S. Cl.
CPC ..... *A61L 2300/414* (2013.01); *A61L 2300/64* (2013.01); *A61L 2430/02* (2013.01); *A61L 2430/06* (2013.01); *A61L 2430/10* (2013.01); *A61L 2430/24* (2013.01); *A61L 2430/30* (2013.01)

(56) References Cited

U.S. PATENT DOCUMENTS

2001/0018567 A1* 8/2001 Bodenschatz ....... A61F 13/0273 602/54
2002/0161400 A1* 10/2002 Demopulos ........ A61B 17/1146 606/215

OTHER PUBLICATIONS

Ashby (1989)—Overview No. 80. On the engineering properties of materials, Acta Metallurgica, 37(5), pp. 1273-1293.
Ashby et al. (1995)—The mechanical properties of natural materials. I. Material property charts, Proc. R. Soc. Lond. A, 450, pp. 123-140.
Avgoulas, Sutcliffe (2016)—Biomimetic-inspired CFRP to perforated steel joints, Composite Structures, 152, pp. 929-938.
Avgoulas, Sutcliffe (2016)—A review of natural joint systems and numerical investigation of bio-inspired GFRP-to-steel joints, Materials, 9(7), pp. 1-22.
Bouten et al. (2014)—The chemistry of tissue adhesive materials, Progress in Polymer Science, 39(7), pp. 1375-1405.
Cox (2002)—The elasticity and strength of paper and other fibrous materials, British Journal of Applied Physics, 3(3), pp. 72-79.
Cummins, Murrell (2003)—Mode of failure for rotator cuff repair with suture anchors identified at revision surgery, Journal of Shoulder and Elbow Surgery, 12(2), pp. 128-133.
Dehaan et al. (2012)—Does Double-Row Rotator Cuff Repair Improve Functional Outcome of Patients Compared With Single-Row Technique?: A Systematic Review, The American Journal of Sports Medicine, 40(5), pp. 1176-1185.
Galatz et al. (2004)—The outcome and repair integrity of completely arthroscopically repaired large and massive rotator cuff tears., The Journal of bone and joint surgery. American volume, 86-A(2), pp. 219-224.
Gelberman et al. (2007)—The Early Effects of Sustained Platelet-Derived Growth Factor Administration on the Functional and Structural Properties of Repaired Intrasynovial Flexor Tendons: An In Vivo Biomechanic Study at 3 Weeks in Canines, Journal of Hand Surgery, 32(3), pp. 373-379.
Genin et al. (2009)—Functional grading of mineral and collagen in the attachment of tendon to bone, Biophysical Journal, 97(4), pp. 976-985.
Graham et al. (2005)—Characterization of a protein-based adhesive elastomer secreted by the Australian frog Notaden bennetti, Biomacromolecules, 6(6), pp. 3300-3312.
Graham et al. (2006)—An adhesive secreted by australian frogs of the genus *Notaden*, in *Biological Adhesives*, p. 207-223.
Harryman et al. (1991)—Repairs of the Rotator Cuff, The Journal of bone and joint surgery. American volume, 73(7), pp. 982-989.
Henkel-Corporation (2014)—Loctite ® 4903™.
Hu et al. (2015)—Stochastic interdigitation as a toughening mechanism at the interface between tendon and bone, Biophysical Journal, 108(2), pp. 431-437.
Inoue et al. (2012)—Effectiveness and biocompatibility of a novel biological adhesive application for repair of meniscal tear on the avascular zone, Science and Technology of Advanced Materials, 13(6), pp. 64219.
Lieber et al. (1996)—Relationship between joint motion and flexor tendon force in the canine forelimb, Journal of Hand Surgery, 21(6), pp. 957-962.
Lieber et al. (1999)—Wrist and digital joint motion produce unique flexor tendon force and excursion in the canine forelimb, Journal of Biomechanics, 32(2), pp. 175-181.
Linderman et al. (2015)—Shear lag sutures: Improved suture repair through the use of adhesives, Acta Biomater, 23, pp. 229-239.
Liu et al. (2012)—Bi-material attachment through a compliant interfacial system at the tendon-to-bone insertion site, Mechanics of Materials, 44, pp. 83-92.
Liu et al. (2014)—Modelling the mechanics of partially mineralized collagen fibrils, fibres and tissue, Journal of the Royal Society, Interface, 11(92), pp. 20130835.
Lo, Ian K. Y., Burkhart (2003)—Double-Row Athroscopic Rotator Cuff Repair: Re-Establishing the Footprint of the Rotator Cuff, Arthroscopy—Journal of Arthroscopic and Related Surgery, 19(9), pp. 1035-1042.
Millar et al. (2009)—Frog glue enhances rotator cuff repair in a laboratory cadaveric model, Journal of Shoulder and Elbow Surgery, 18(4), pp. 639-645.
Nairn (1997)—On the use of shear-lag methods for analysis of stress transfer in unidirectional composites, Mech, 26, pp. 63-80.
Oh et al. (2007)—Indications for rotator cuff repair: a systematic review, Clinical orthopaedics and related research, 455(455), pp. 52-63.
Patel et al. (2016)—Advances in biologic augmentation for rotator cuff repair, Annals of the New York Academy of Sciences, 1383(1), pp. 97-114.
Pedowitz et al. (2011)—Optimizing the management of rotator cuff problems., The Journal of the American Academy of Orthopaedic Surgeons, 19(6), pp. 368-379.
Silva et al. (2006)—Early healing of flexor tendon insertion site injuries: Tunnel repair is mechanically and histologically inferior to surface repair in a canine model, Journal of Orthopaedic Research, 24(5), pp. 990-1000.
Thomopoulos et al. (2012)—Effect of bone morphogenetic protein 2 on tendon-to-bone healing in a canine flexor tendon model, Journal of Orthopaedic Research, 30(11), pp. 1702-1709.
Thomopoulos et al. (2003)—Variation of biomechanical, structural, and compositional properties along the tendon to bone insertion site, Journal of Orthopaedic Research, 21(3), pp. 413-419.
Thomopoulos et al. (2009)—Use of a Magnesium-Based Bone Adhesive for Flexor Tendon-to-Bone Healing, Journal of Hand Surgery, 34(6), pp. 1066-1073.
Vorys et al. (2015)—Optimal internal fixation of anatomically shaped synthetic bone grafts for massive segmental defects of long bones, Clinical Biomechanics, 30(10), pp. 1114-1118.
Wegst, Ashby (2004)—The mechanical efficiency of natural materials, Philosophical Magazine, 21(21), pp. 2167-2181.
Yamaguchi (2011)—New guideline on rotator cuff problems, AAOS Now, 5, pp. 1-3.

\* cited by examiner

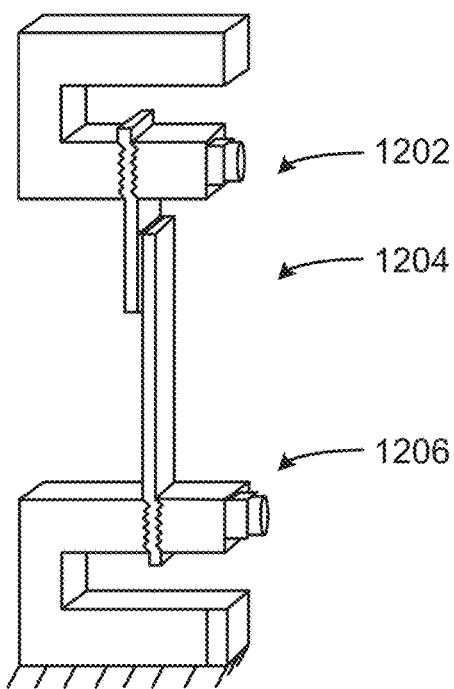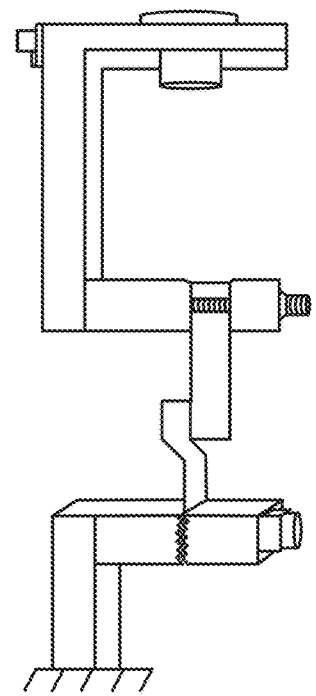
FIG. 12A    FIG. 12B
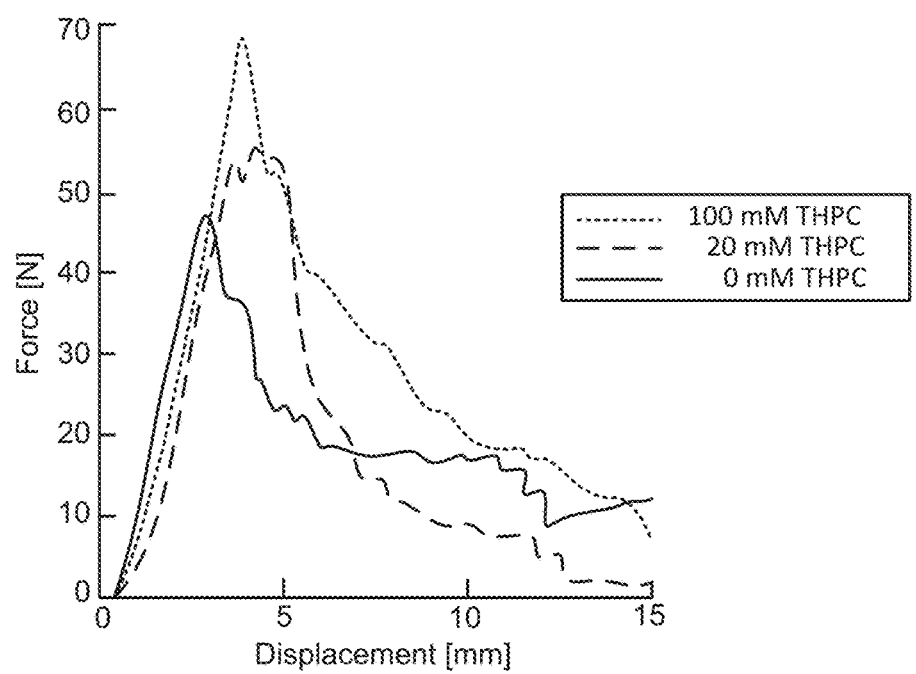
FIG. 12C

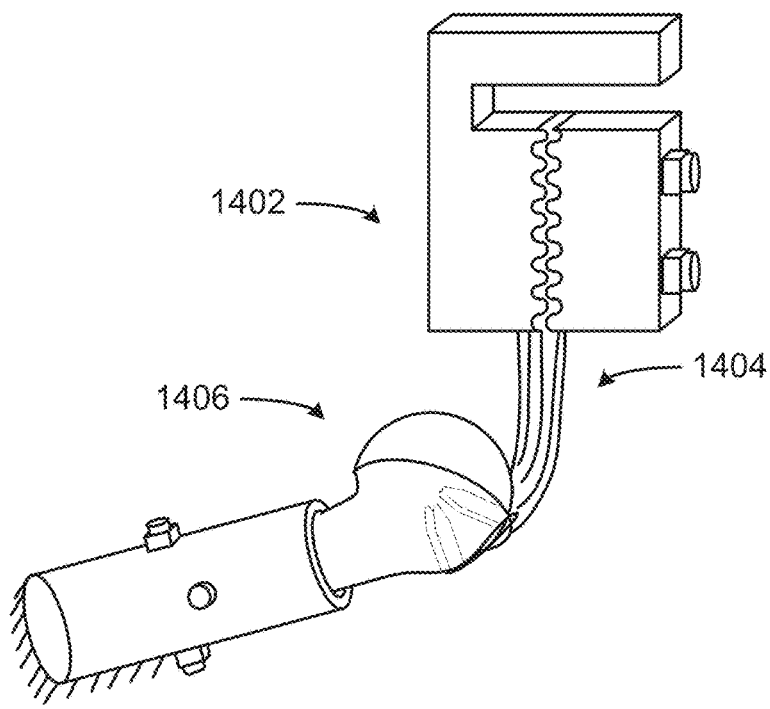
FIG. 14A
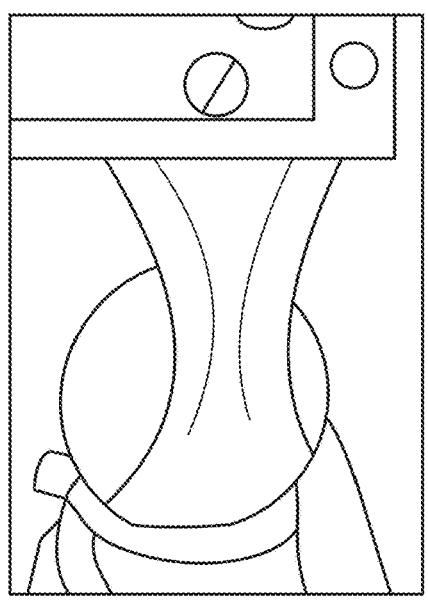 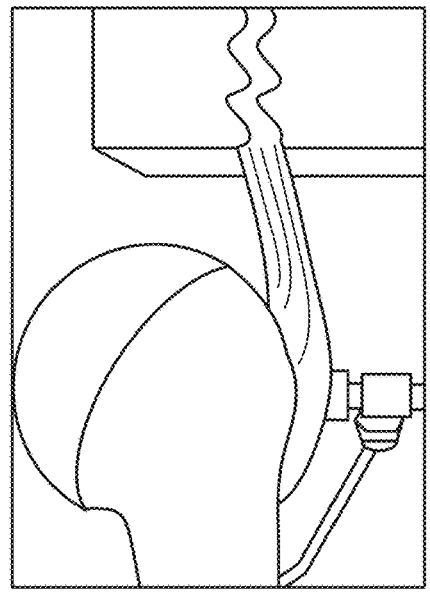
FIG. 14B　　　　　　FIG. 14C

COMPOSITIONS AND METHODS FOR TISSUE REPAIR

CROSS-REFERENCE TO RELATED APPLICATIONS

This application claims priority from U.S. Provisional Application Ser. No. 62/309,214 filed on 16 Mar. 2016 and is a Continuation-in-Part of U.S. application Ser. No. 14/940,541 filed Nov. 13, 2015, which claims priority from U.S. Provisional Application Ser. No. 62/079,965, filed Nov. 14, 2014, which are incorporated by reference in their entireties.

STATEMENT REGARDING FEDERALLY SPONSORED RESEARCH OR DEVELOPMENT

This invention was made with government support under AR060719, GM007200, and AR062947 awarded by the National Institutes of Health. The government has certain rights in the invention.

MATERIAL INCORPORATED-BY-REFERENCE

Not Applicable.

FIELD OF THE INVENTION

The present disclosure generally relates to compositions and methods for repairing tissue defects.

BACKGROUND OF THE INVENTION

Surgical repair of tissue defects, such as tears in soft tissue and tears of the attachments of soft tissues to bone, are typically accomplished via techniques based upon suturing. A common post-surgical complication is a failure of the sutures to keep the healing surfaces in contact with one another. Common failure mechanisms include tearing of the soft tissue near the suture anchor points, failure of the sutures, and sliding of the healing surfaces relative to one another.

As an example, repair of tendon/ligament to bone is a difficult challenge in orthopedic surgery. For example, there are approximately 600,000 rotator cuff surgeries annually in the US alone. Surgical repair of the rotator cuff requires re-attachment of tendon to bone. However, attachment of dissimilar materials such as tendon and bone is mechanically challenging due to stress concentrations that arise at their interface. As a result, current approaches for rotator cuff repair are largely unsuccessful, with 20-94% failure rates. The two primary reasons for failed repair are: (1) poor initial mechanical fixation of the tendon and bone, and (2) a lack of regeneration of the native tendon-to-bone attachment structure. Similarly, re-attachment is a clinical challenge in other load-bearing tissues as well, including anterior cruciate ligament reconstruction, meniscus repair, and Achilles tendon repair.

To continue with the example of tendon to bone repair, the current standard of care for repairing a torn rotator cuff consists of grasping the tendon with suture and securing it to the bone using anchors. This results in load transfer from tendon to bone across the few anchor points and a high risk of failure at the tendon-suture or tendon-anchor interface. Furthermore, current care does not include any biologic augmentation at the repair site, and the typically poor healing at the tendon-bone interface is insufficient to mechanically integrate the tendon to the bone. A number of biologic grafts have been tested clinically for enhancing rotator cuff repair, but none have shown efficacy. Current grafts have been unsuccessful primarily due to their use as patches over the repair site (i.e., there are not interposed between the healing tendon and bone) and their poor mechanical properties.

SUMMARY OF THE INVENTION

Among the various aspects of the present disclosure is the provision of a composition and method for tissue defect repair. Briefly, therefor, the present disclosure is directed to repairing tissue defects involving tissue to tissue (e.g., tissue to bone) interfaces.

The present teachings include compositions for repairing tissue defects involving tissue to bone interfaces. In accordance with a further aspect, the composition can comprise a film and an adhesive, a sticky film, or an adhesive layer.

The present teachings include methods for repairing tissue defects involving tissue to bone interfaces. In accordance with a further aspect, the method can include providing a film or an adhesive layer; contacting the film with an adhesive agent or contacting the adhesive layer; delivering the film or the adhesive layer to a tissue defect; and applying an adhesive to the film or directly to the tissue.

The present teachings include methods of surgical repair of a tissue defect. In accordance with a further aspect, the tissue defect includes a first tissue and a second tissue, including: connecting a first tissue and second tissue in a subject; implanting a film into a subject in need thereof; or connecting a first tissue to a second tissue with an anchored suture, wherein the film is implanted between the first tissue; and the film comprises an adhesive.

In accordance with a further aspect, the compositions and methods include a film comprising an adhesive.

In accordance with a further aspect, the compositions and methods include a suture or an adhesive coated suture, a cell or cell sheet comprising a cell, a growth factor, a hydrogel, or a polymer.

In accordance with yet another aspect, the compositions and methods include the hydrogel or polymer is a delivery agent for the adhesive, growth factor, or cell; the growth factor is delivered by a hydrogel-based delivery system, a microsphere-based delivery systems, or a fibrin-based delivery system; the cell is seeded directly onto or into the film or the layer; the suture or the anchor comprises an adhesive; the adhesive is delivered by a porous suture; the growth factor is CTGF/CCN2; the cell or cell sheet comprises a cell selected from the group consisting of: a living cell, a population of cells, a mesenchymal stromal cell, a tendon-derived stem cell, and an adipose-derived progenitor; the hydrogel or polymer is interspersed with an adhesive, a growth factor, or a cell; the composition is structured randomly or tailored to specify or optimize a strength, a toughness, or a stiffness of the adhesive or repair; or the adhesive is coated upon or applied to either the tissue or the suture prior to or during repair.

In accordance with yet another aspect, the compositions and methods include the polymer or the hydrogel as a structure to deliver adhesive, growth factor, or cells; the suture or the anchor comprising of an adhesive; the adhesive delivered by porous sutures; the hydrogel or polymer interspersed with an adhesive, a growth factor, or a cell; or the composition is structured randomly or tailored to specify or optimize a strength, a toughness, or a stiffness of the adhesive or repair.

In accordance with yet another aspect, the compositions and methods include an adhesive film or adhesive layer at a tissue defect site that increases post-surgical strength at the tissue defect site; increases strength at the tissue defect site; reduces post-surgical failure; results in improved healing; results in improved surgical outcome; improves load transfer; increases the strength of a tissue defect repair; reduces time for healing of a tissue defect repair; shifts the load from a few anchor points to shear along the entire adhesive film or adhesive layer, minimizing stress concentration at a repair site; a repaired tissue defect site comprising sutures and the film or the layer has an increased strength compared to a repaired tissue defect site with no film or the layer used; or has at least a 20% increase in strength compared to a repaired tissue defect site with no film or the layer used.

In accordance with yet another aspect, the compositions and methods include the tissue defect is selected from the group consisting of a musculoskeletal injury, a connective tissue-to-bone defect, a connective tissue-to-connective tissue defect, a ligament-to-bone tissue defect, or a tendon-to-bone tissue defect; a ligament/tendon-to-bone insertion, an articular cartilage-to-bone junction, a hip labrum, an intervertebral disc, a nucleus pulposus-annulus fibrosus-endplates, a cementumperiodontal ligament-alveolar bone, a muscle-to-tendon, an inhomogeneous or anisotropic tissue, a knee meniscus, a temporomandibular joint disc, a root-periodontium complex, a tendon-bone insertion, a synovial joint, or a fibrocartilaginous tissue; or a flexor tendon, a rotator cuff, an anterior cruciate ligament, a meniscus, or an Achilles tendon.

In accordance with yet another aspect, the compositions and methods include a film comprising one or more selected from the group consisting of a biocompatible film, a polymer nanofiber mesh, an ionic polymer layer, an ionic polymer film, a biodegradable polyester film, a polysaccharide-based film, a polysaccharide-based hydrogel, a polyester film, or a collagen-based matrix, a spacer material, and patterning thereof.

In accordance with yet another aspect, the compositions and methods include an adhesive comprising one or more selected from the group consisting of: a catechol-based adhesive, a DOPA-based adhesive, a mechanically-based adhesive, a fibrin-based adhesive, bioglue, an ionic polymer adhesive, a biodegradable polyester adhesive, and a polysaccharide-based adhesive; an adhesive having a shear modulus ($G_a$) between about $10^3$ and $10^{10}$ Pa; or an adhesive failure shear stress value is greater than about $10^5$ Pa.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

FIG. 2A illustrates the front view of adhesive suture in tendon 200A comprising a tendon repair interface 202 and an anchor point 204. FIG. 2B is an illustration of the crossectional view of adhesive suture in tendon 200B showing the tendon 206, the adhesive 208, and the suture 210. FIG. 2C illustrates the right half view of adhesive suture in tendon 200C.

FIG. 4A is a graph of forces required for suture pullout using a variety of adhesive coatings on suture within cadaver canine flexor tendon. FIG. 4B is a schematic showing the test setup and dimensions. FIG. 4C is a representative example force-strain curve for a single strand pullout test using Loctite 4903-coated suture.

FIG. 5A is a schematic showing the mechanical test setup and dimensions (distal phalynx 502; repaired flexor tendon 504). FIG. 5B is a box plot of forces required for cadaver canine flexor tendon repair failure using control repairs without adhesive (green) vs. repairs with Loctite 4903-coated suture (blue). FIG. 5C is a representative example force-strain curve for a clinically-relevant repair mechanical test using Loctite 4903-coated suture.

FIG. 6A is an illustration showing a standard repair (no adhesive) 600A and stress concentrations at anchor 602. FIG. 6B is an illustration showing an adhesive film interposed at insertion 600B and stress distribution over footprint 604.

FIG. 7A illustrates a tendon to bone attachment, tendon 206, adhesive 208, and bone 702. FIG. 7B is a cross section of FIG. 7A showing tendon 206, adhesive 208, and bone 702. FIG. 7C is a free body diagram (FBD) of section repair showing tendon 206, adhesive 208, and bone 702.

FIG. 9A is predicted from shear lag modeling, and FIG. 9B is predicted from finite element modeling of a two dimensional idealized tendon-to-bone repair with an adhesive layer. Compliant adhesives distribute stress to the tendon over a longer length. The finite element model corroborates shear lag modeling for adhesives more compliant than 1 GigaPascal, especially for the peak shear stress at the edges of the adhesive layer.

FIG. 10A is predicted from shear lag modeling, and FIG. 10B is predicted from finite element modeling of a two dimensional idealized tendon-to-bone repair with an adhesive layer. Compliant adhesives distribute stress to the tendon over a longer length. The finite element model corroborates shear lag modeling for adhesives more compliant than 1 GigaPascal.

FIG. 12A-FIG. 12C are a series of illustrations and images demonstrating mechanical testing of adhesives interposed between tendon and bone planks in order to rapidly evaluate adhesive mechanical properties using relevant adherends. FIG. 12A is a schematic showing a bone plank 1202, an adhesive junction 1204, and a tendon plank 1206. FIG. 12B is a schematic of the biomechanical testing setup for idealized single lap shear experiments using tendon and bone planks as adherends. FIG. 12C shows representative force displacement curves using multipartite adhesives comprised of cyanoacrylate and 1/16 inch thick tendon planks treated with various concentrations of tetrakis (hydroxymethyl) phosphonium chloride (THPC).

FIG. 13A shows elastic modulus of ⅛ inch thick THPC treated tendon planks tested in tension (no adhesive or repair). (FIG. 13B) Shear modulus, (FIG. 13C) maximum shear stress, and (FIG. 13D) yield stress ($\tau_{ave}$) are shown for multipartite adhesives evaluated in idealized lap shear tests and cadaver infraspinatus tendon insertion repairs. Stronger adhesive materials (100 milliMolar THPC-crosslinked) failed at 52% greater average shear stress. The middle line within the box plots represents the median, the outer edges denote the 25 percentile and 75 percentile samples, and the whiskers extend to the extreme data points. Outliers are denoted by (+). Asterisks denote statistically significant differences compared to idealized lap shear tests for 0 milliMolar THPC group (*p<0:05, p<0:01, *p<0:001, & p=0:064).

FIG. 14A-FIG. 14C are a series of illustrations, images, and graphs depicting the experiment and data from a human cadaver rotator cuff tendons repaired to the humeral head with adhesive only (infraspinatus), double-row suture only (supraspinatus), or adhesive and suture (supraspinatus). (FIG. 14A) Schematic drawing of biomechanical testing setup for clinically relevant repairs including a freezing grip 1402, supraspinatus 1404, and a humerus 1406. (FIG. 14B) Front view and (FIG. 14C) side view illustrations of biomechanical tests.

FIG. 16A is an illustrations showing tendon structured, porous adhesive bone 1602. FIG. 16B is an illustrations showing a too stiff bioactive sheet where the stress concentration 1604 is at the intersection of the tendon and the bioactive sheet. FIG. 16C is an illustration showing optimized bioactive sheets where the stress concentration relieved and a stress-driven soluble factor can be released 1606. FIG. 16D is an illustration showing a too compliant bioactive sheet where there can be instantaneous soluble factor release 1608.

FIG. 17 shows a porous suture 1702, an adhesive solution or a biofactor solution 1704, a porous suture loaded with adhesive or biofactor 1706, FDP tendon repair with loaded porous suture 1708, skin 1710, sheath 1712, tendon 1714, and transection 1716. Porous sutures enable increased adhesive loading capacity, and provide increased surface area for adhesive binding. Porous suture creation was demonstrated previously by the inventors and collaborators (Li et al, *Advanced Materials*. 2016 June; 28(23):4620-4. doi: 10.1002/adma.201506242). This patent envisions application of adhesive-coated sutures using porous suture technology as one example application.

DETAILED DESCRIPTION OF THE INVENTION

Figure 1A:
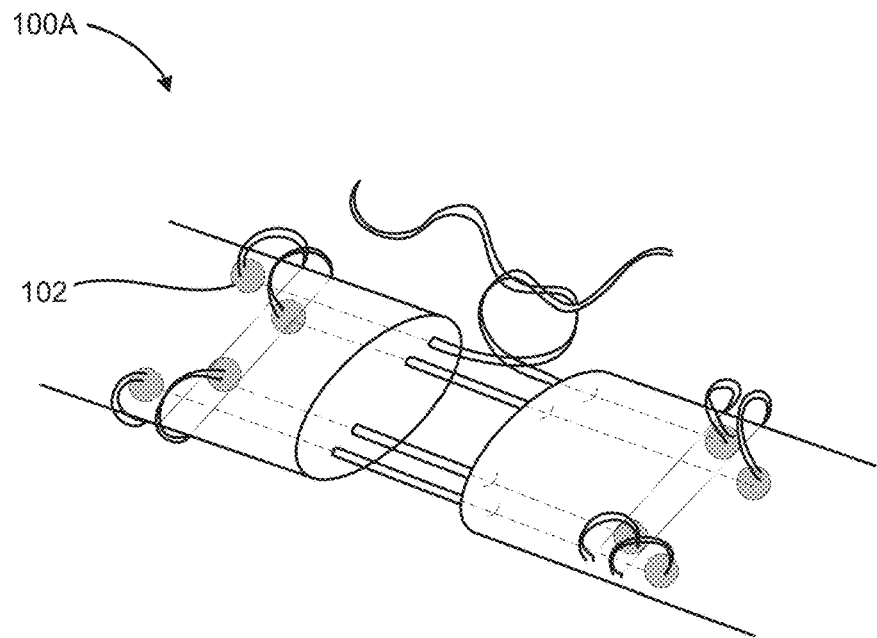
FIG. 1A-FIG. 1B show approximate stress distributions for standard clinical tendon repairs 100A (FIG. 1A) versus repairs augmented with adhesive-coated sutures 100B using mechanically optimized, adhesive biomaterials (FIG. 1B). An 8-stranded Winters-Gelberman suture repair technique is shown for human flexor digitorum profundus tendon repair as an example surgical tendon repair for illustrative purposes. Current suturing techniques generate stress concentrations at anchor points 102 where the suture bends within tissue. Adhesive-coated sutures distribute that load transfer along the length of the suture 104, increasing the surface area for load transfer and reducing peak stresses and improving overall repair mechanics. Red shading indicates the stress and the location of load transfer.
Figure 1B:
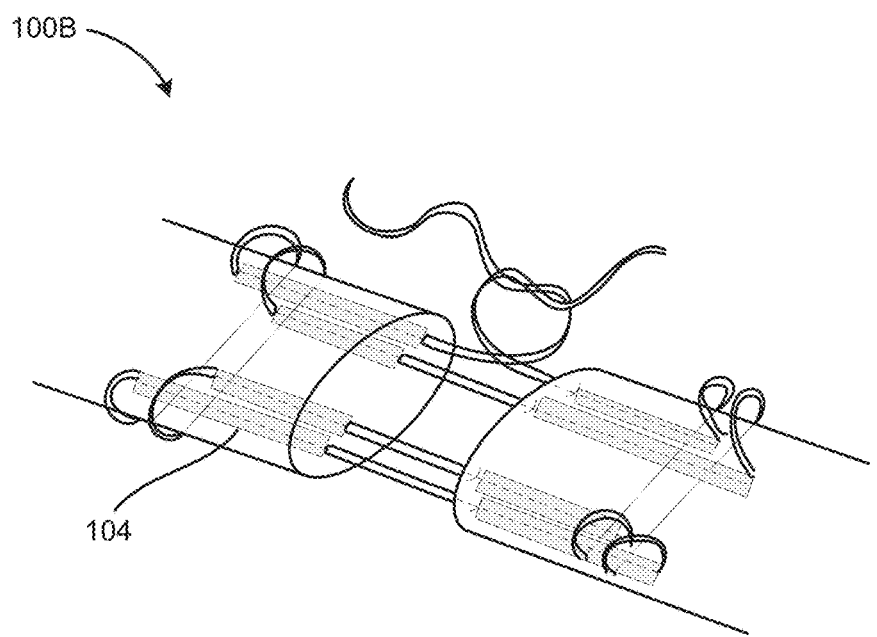
Figure 2A:
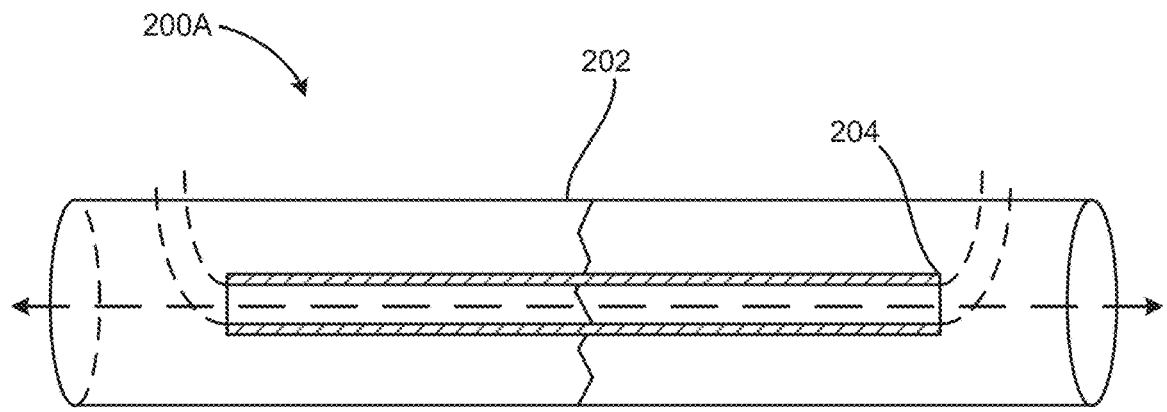
FIG. 2A-FIG. 2C is a series of schematics demonstrating an adhesive-coated suture within a cylindrical tissue, such as tendon, used to conduct shear lag analysis. $P_s$ is the tensile load carried by the suture at the interface between repaired tissues (i.e., at x=0). Adhesive-coated sutures with optimized mechanical properties allow us to maximize this load. The variables represent: t=thickness, E=Young's modulus, G=shear modulus, σ=normal stress, and τ=shear stress at various positions x along the insertion from x=(0, L).
Figure 2B:
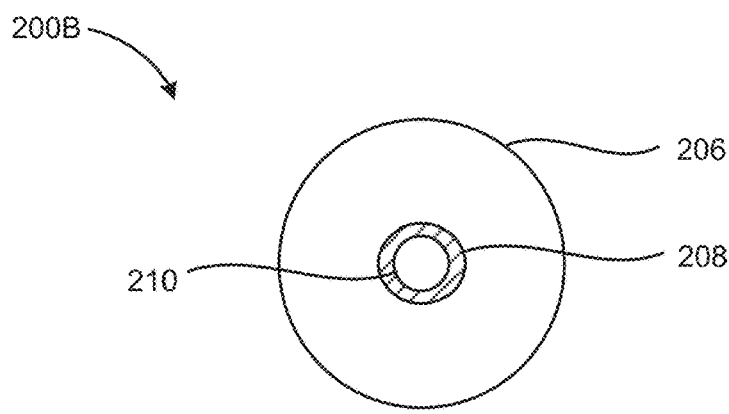
Figure 2C:
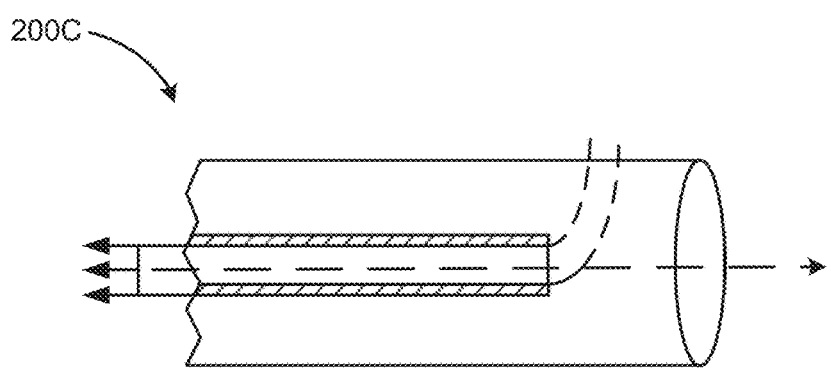
Figure 3:
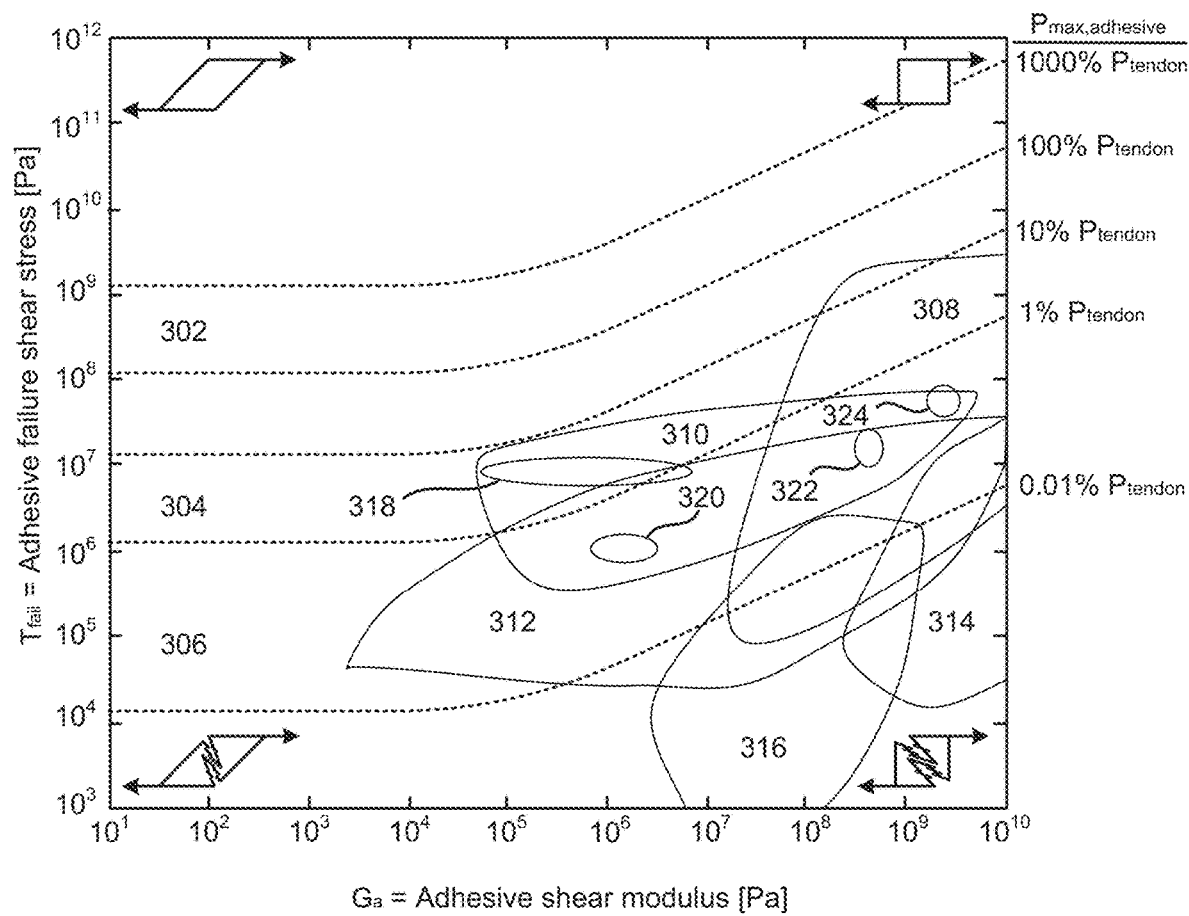
FIG. 3 is a contour map showing the design space for adhesive biomaterials for use in adhesive-coated sutures, using the human flexor digitorum profundus tendon repair parameters as an example of one such repair in order to calculate relevant values. The x-axis shows the shear modulus of the adhesive material, y-axis shows the shear stress at which the adhesive material fails, and the contours show the total maximum force transferred across the repair site via the adhesive, normalized by the strength of an uninjured tendon ($P_{tendon}$). This domain map is overlaid with real material properties to highlight promising materials for further adhesive development. Experimental results indicate that adhesives provide an additive improvement compared to the suture repair without adhesives. The contour map illustrates areas of repair strength increase limited by suture strength 302, repair strength increase 304, and limited benefit-adhesive fails before current repair 306. Real materials overlaid on this map include fibres and particulates 308, elastomers 310, foams 312, ceramics 314, honeycombs 316, styrene butadiene rubber (latex-rubber cement) 318, polychloroprene (Neoprene) 320, flexible Cyanoacrylate 322, and nylon 6.6 324.
Figure 4A:
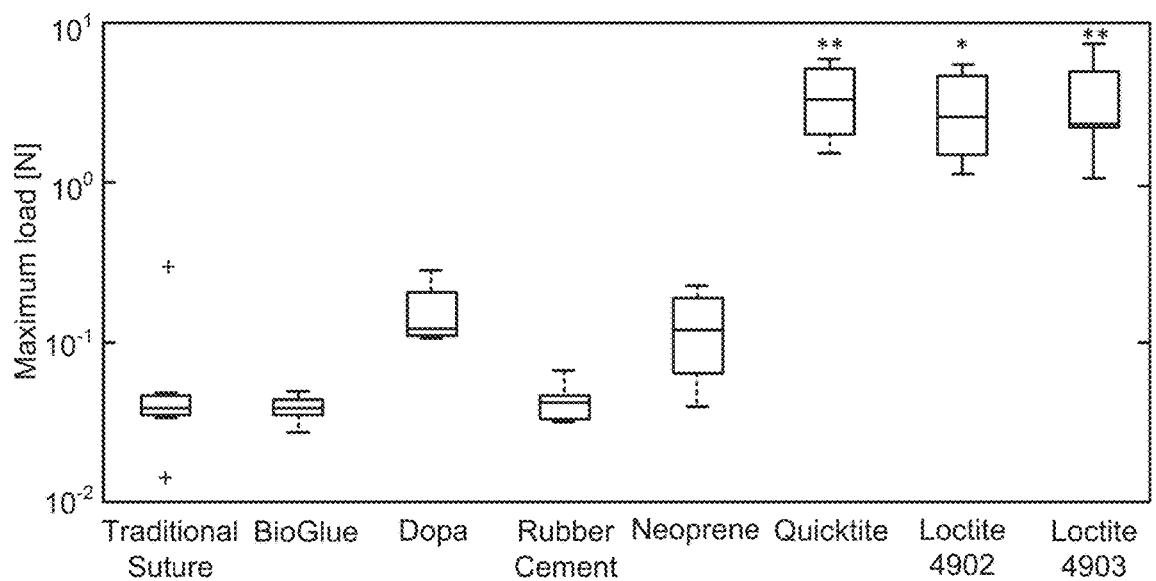
FIGS. 4A-FIG. 4C show validation of shear lag modeling of adhesive-coated sutures using a single strand pullout test.
Figure 4B:
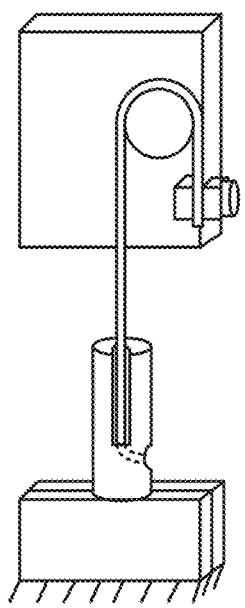
Figure 4C:
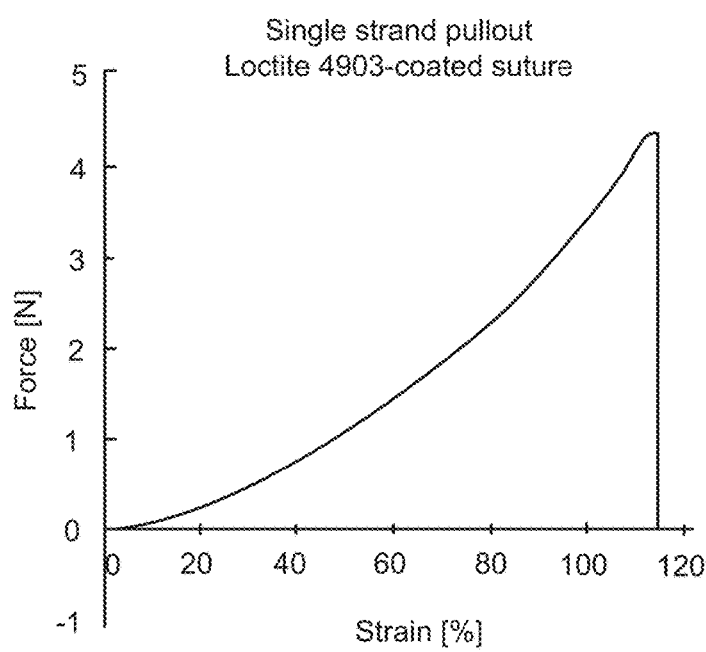
Figure 5A:
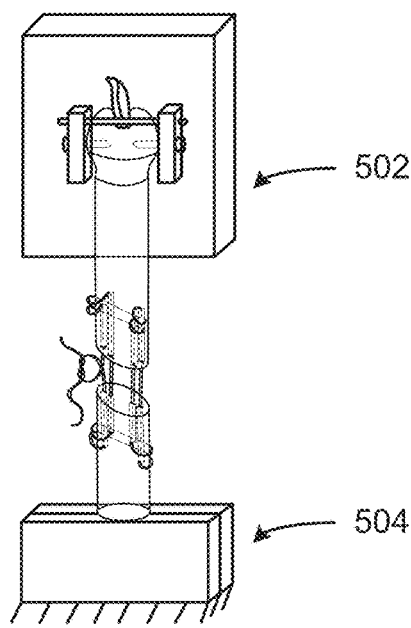
FIG. 5A-FIG. 5C show validation of shear lag modeling of adhesive-coated sutures using a clinically-relevant flexor digitorum profundus tendon repair.
Figure 5B:
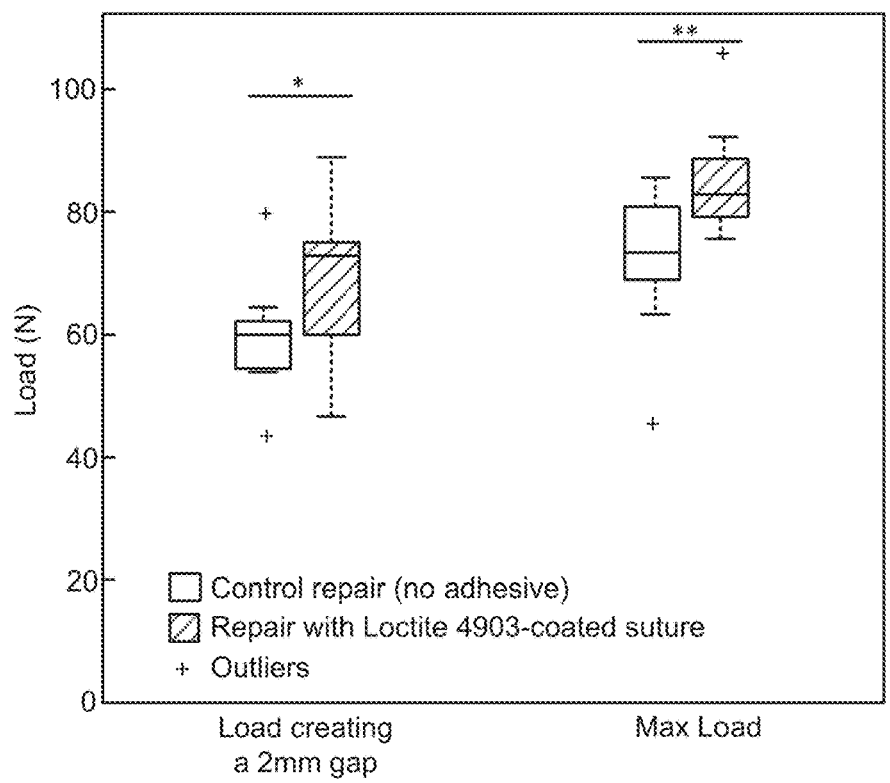
Figure 5C:
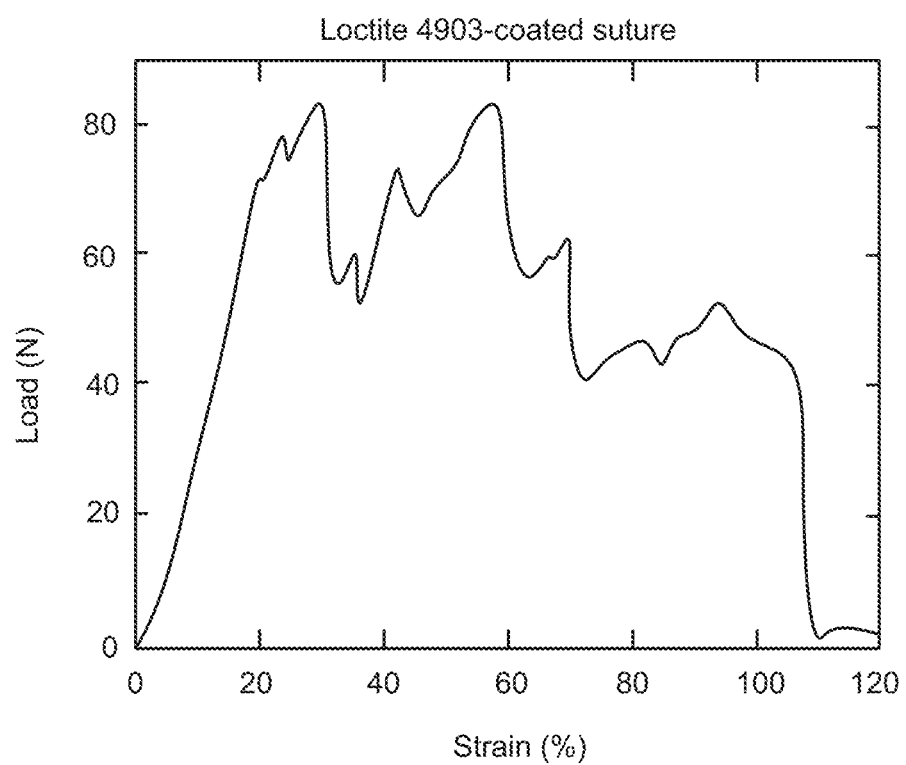

Tendon-to-bone surgical repairs fail to recreate the load transfer mechanisms of the native enthesis, leading to unacceptably high repair failure rates. Instead of using a footprint area to distribute load, repairs concentrate stress on only a small number of points where sutures connected to bone anchors penetrate through tendon tissue. Expanding on the approach described in our previous work to distribute load over the length of adhesive-coated sutures (U.S. patent application Ser. No. 14/940,541, incorporated herein by reference, upon which this application is a Continuation-in-Part), here, it is disclosed that mechanically-optimized adhesive films can mimic the natural load transfer mechanisms of an enthesis, increasing the load tolerance of the repair. The present disclosure is based, at least in part, on the discovery that films comprising an adhesive can increase the strength of a tendon to bone repair. As shown herein, ~20% improved strength was measured in 6 human shoulder experiments (see e.g., Example 4).

The concept of enhanced repair strength through improved load distribution is broadly applicable across various surgical repair scenarios. Here, adhesion was added to repair sites with relatively large attachment areas, such as those typical seen in tendon-to-bone repair. Although these repairs have the potential to transfer high loads across a relatively large surface, current surgical repair techniques continue to rely on load transfer concentrated across a small number of suture anchor points. As described here, adhesive application to tendon-to-bone repairs was investigated in order to improve strength across the tendon-to-bone repair site.

Tissue Defect

The compositions and methods as described herein can be used to treat a tissue defect. As described herein, a tissue defect can be a tissue-to-tissue defect, for example, a ligament/tendon-to-bone injury, connective tissue to bone, connective tissue to connective tissue, or a musculoskeletal injury. A repair of the tissue defect site can be strengthened with the use of a film as described herein. Repair of tendon/ligament to bone has been shown to be a difficult challenge in orthopedic surgery.

A tissue defect that can be treated with the compositions and methods as described herein can be any injury resulting from damage of tissue at tissue defect site or at the interface of the muscle and skeleton, which can be due to a strenuous activity.

Methods, systems, and compositions described herein can provide support for surgical and tissue defect/injury sites in tissue-tissue interfaces and multi-tissue interfaces, including but not limited to ligament/tendon-to-bone insertion, articular cartilage-to-bone junction, hip labrum, intervertebral disc (nucleus pulposus-annulus fibrosus-endplates), cementum-periodontal ligament-alveolar bone, muscle-to-tendon, inhomogeneous or anisotropic tissues such as knee meniscus or temporomandibular joint disc, root-periodontium complex, tendon-bone insertion, synovial joints, or fibrocartilaginous tissues.

Repair of the tissue defects listed above, especially tendon-to-bone repair, presents a challenging mechanical problem: repairs require high strength and resilience to accommodate forces from activities of daily living and to avoid repair site elongation or rupture; however, the bond between compliant tendon and stiff bone causes high stress concentrations that limit attachment strength.

TABLE 1

Abbreviations and variables

| | | | |
|---|---|---|---|
| PBS | phosphate buffered saline | THPC | tetrakis (hydroxymethyl) phosphonium chloride |
| x | position along adhesive lap | L | adhesive lap length |
| $\tau(x)$ | shear stress in the adhesive layer | $\tau_{ave}$ | average shear stress, i.e., P/wL |
| $\tau_{fail}$ | failure shear stress of adhesive | $\sigma_t(x)$ | normal stress in tendon normalized by normal stress at x = 0 |
| $E_b$ | bone elastic modulus | x/L | position along adhesive lap normalized by lap length |
| $E_t$ | tendon elastic modulus | $E_t^*$ | tendon elastic modulus normalized by bone elastic modulus |
| $G_a$ | adhesive shear modulus | $G_a^*$ | adhesive shear modulus normalized by bone elastic modulus |
| $t_t$ | tendon thickness | $t_t^*$ | tendon thickness normalized by bone elastic modulus |
| $t_a$ | adhesive thickness | $t_a^*$ | adhesive thickness normalized by bone thickness |
| $t_b$ | bone thickness | P | normal force across joint far from insertion, i.e., x = 0 and x = L |
| $P_{max}$ | force P causing joint failure | $L_{intersect}$ | lap length where asymptotic limits for load transfer intersect |
| X | variable related to geometry and material properties | B | characteristic (inverse) length scale related to geometry and material properties |

The healthy tendon enthesis facilitates load transfer from tendon to bone in several ways, including by (i) distributing force over a relatively large footprint area to reduce local stresses, (ii) using a compliant transitional fibrocartilaginous tissue to optimize stress concentrations and toughen the attachment, and (iii) interdigitating fibrocartilage with bone. Unfortunately, current surgical repair techniques fail to recreate these stress-dissipation mechanisms, leading to high failure rates.

Rotator cuff injury is one example of a tendon-to-bone injury that is notoriously challenging to repair. Post-repair rupture rates range from 20% for young, healthy athletes with small tears to as high as 94% for massive tears in elderly patients. These failure rates are not surprising from a mechanical perspective: single- and double-row rotator cuff repairs transfer almost all of the force from muscle to bone across two anchor points, where the suture from a bone anchor punctures through the tendon. The vast majority (86%) of rotator cuff repair ruptures occur by the tendon pulling through the sutures at those anchor points. Due to these high failure rates, operative rotator cuff repair is only indicated for a subset of patients with symptomatic (i.e., painful) shoulders. In other words, repairs can be performed to reduce pain without reinstating shoulder function. Approximately half of the US population over 60 years old has a rotator cuff tear, leading to over 500,000 repairs of symptomatic shoulders annually. Approximately $500 million per year is spent on repairs that rupture. With a growing aging and elderly population, improving on these failure rates is critical to reinstate shoulder function in these patients.

While there have been many improvements in surgical technique for rotator cuff repair over the last several decades, the current standard of care using suture and anchors can be a crude mechanical solution. The current standard of care for repairing a torn rotator cuff consists of grasping the tendon with suture and securing it to the bone using anchors. This results in load transfer from tendon to bone across the few anchor points and a high risk of failure at the tendon-suture or tendon-anchor interface. Similar to the motivation for adhesive-coated sutures in U.S. patent application Ser. No. 14/940,541, incorporated herein by reference, this work was motivated partially because the current repair approaches do not typically use the length of suture or the attachment area effectively to transfer load.

Furthermore, current care does not include any biologic augmentation at the repair site, and the typically poor healing at the tendon-bone interface is insufficient to mechanically integrate the tendon to the bone. A number of biologic grafts have been tested clinically for enhancing rotator cuff repair, but none have shown efficacy. Current grafts have been unsuccessful primarily due to their use as patches over the repair site (i.e., there are not interposed between the healing tendon and bone) and their poor mechanical properties.

As another example, there are approximately 10,000 flexor tendon repairs annually (USA). Furthermore, the elongation rate is 48% and the rupture rate is 6-10%. Most failures happen within first 6 weeks.

The two primary reasons for failed repair are: (1) poor initial mechanical fixation of the tendon and bone, and (2) a lack of regeneration of the native tendon-to-bone attachment structure. Similarly, re-attachment is a clinical challenge in other load-bearing tissues as well, including anterior cruciate ligament reconstruction, meniscus repair, and Achilles tendon repair.

To address these issues, the present disclosure provides an adhesive film that has the capability to deliver cells or growth factors to the repair. The adhesive properties increase the initial attachment strength of the tendon-to-bone repair by reducing local elevations of stress, and the cells and growth factors can enhance the biology of tendon-to-bone healing. While the experiments described in the present disclosure are focused on the rotator cuff, it is understood that the disclosure can be readily applied to other anatomical sites in orthopedics (e.g., anterior cruciate ligament reconstruction, meniscus repair, Achilles tendon repair) as well as other surgical specialties (e.g., hernia repair, skin closure).

As mentioned above, 20-94% of rotator cuff repairs fail, primarily due to poor fixation of the tendon to the bone. The adhesive films disclosed herein can reduce this failure rate, leading to significantly fewer revision surgeries by applying fixation across the entire tendon-to-bone footprint area. The adhesive films disclosed herein result in improved mechanical fixation of tendon to bone, delivery of bioactive factors for enhanced healing, and delivery of cells for enhanced healing.

Currently, the critical period for tendon repair is in the first 6 weeks. An adequate mechanical solution needs to hold the tendon together for long enough (about 6 weeks) for a body to heal sufficiently. A suture or suture anchor system can be a crude mechanical solution that does not use the length of the suture to transfer load most effectively.

Figure 9A:
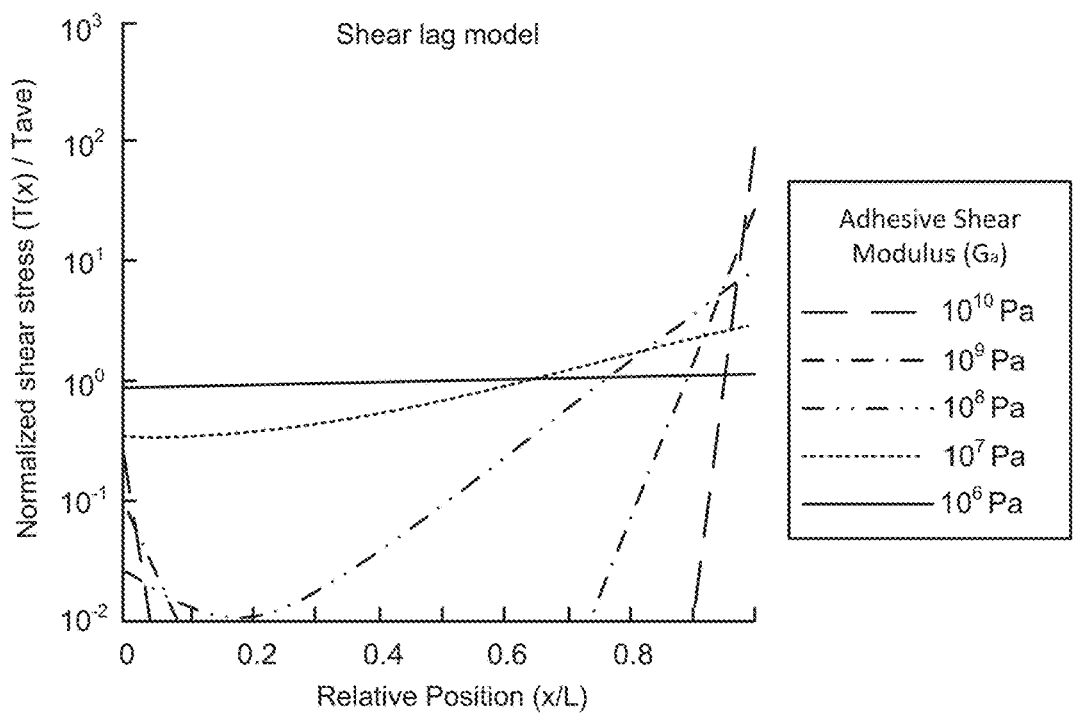
FIG. 9A-FIG. 9B show the expected shear stress in the adhesive layer or adhesive film vs. position, normalized, for a tendon-to-bone repair using an adhesive film with a range of adhesive shear moduli from 100 kiloPascals to 1 GigaPascal.
Figure 9B:
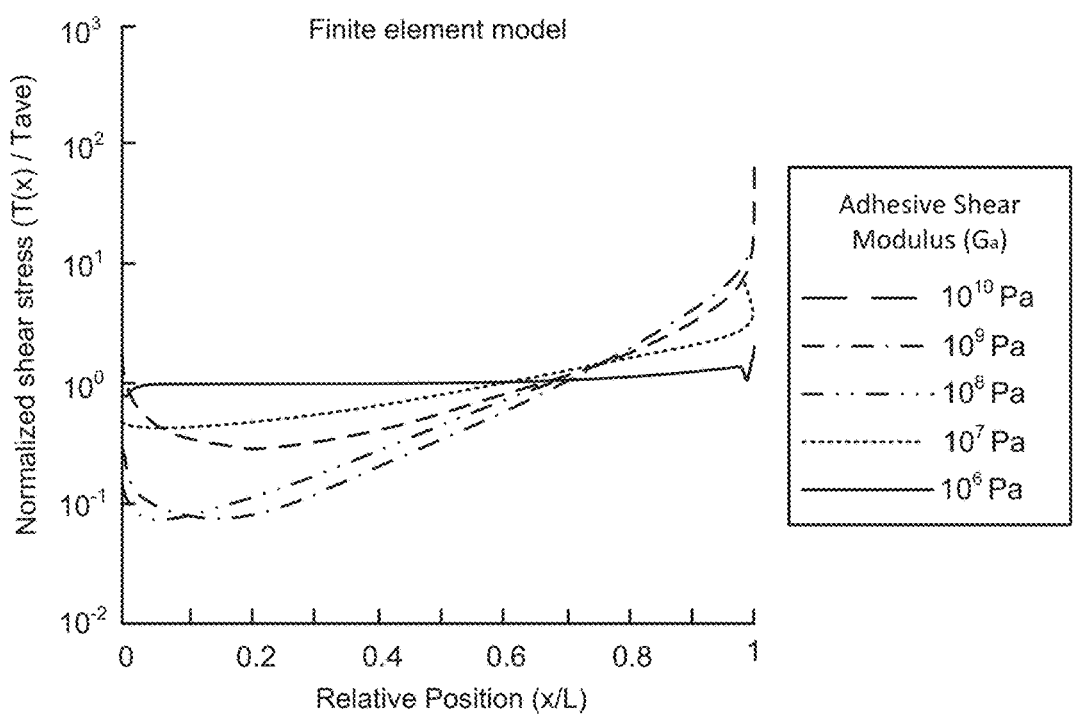
Figure 10A:
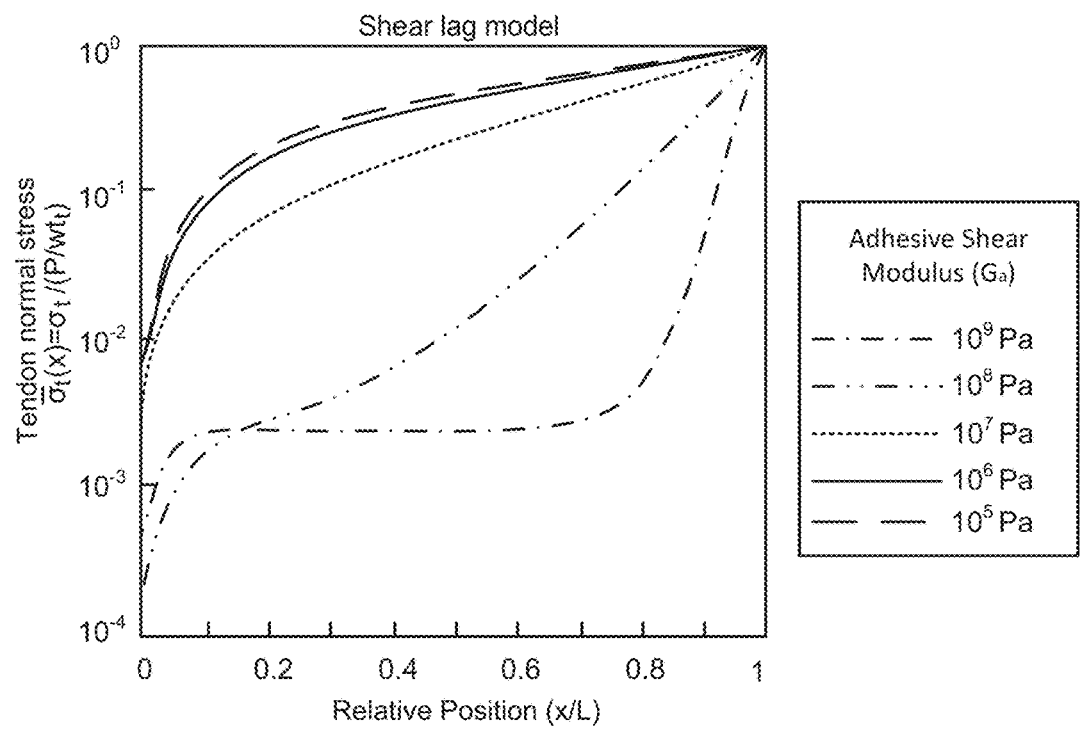
FIG. 10A-FIG. 10B show the expected normal stress in a tendon vs. position, normalized, for a tendon-to-bone repair using an adhesive film with a range of adhesive shear moduli from 100 kiloPascals to 1 GigaPascal.
Figure 10B:
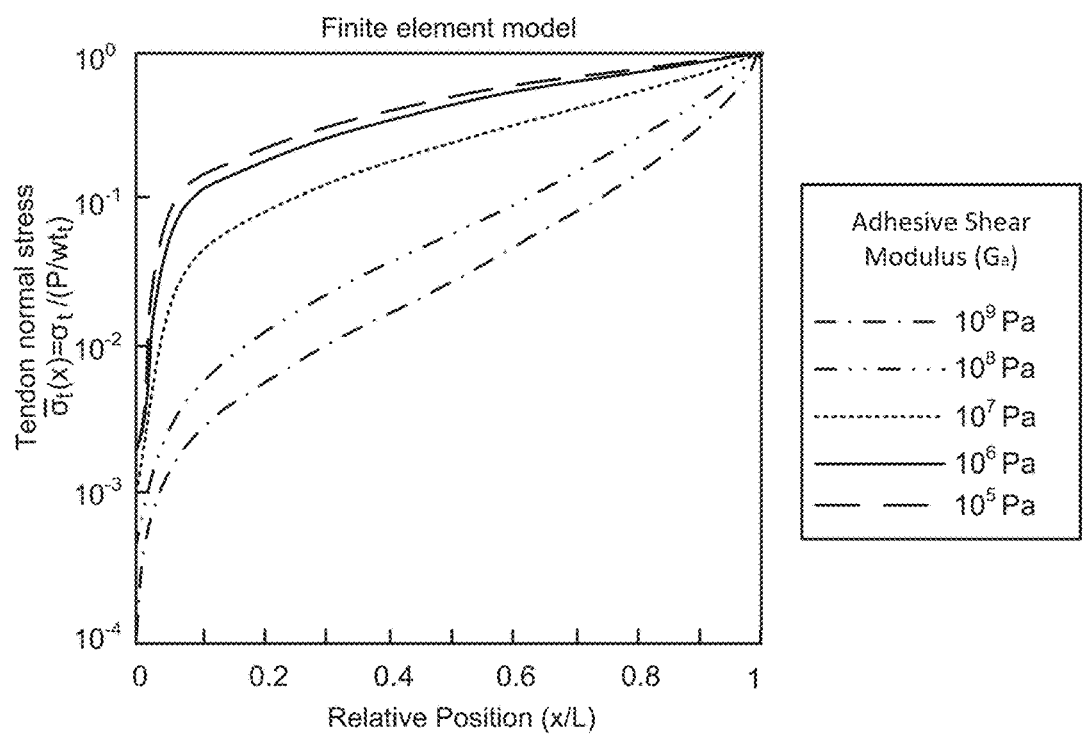

Here, an adhesive-film based approach is shown to augment standard tendon-to-bone repairs. This adhesive-based surgical augmentation mimics the natural stress distribution across the repair site to improve repair strength and limit ruptures. Unlike conventional suture repairs with only a few anchor points, this adhesive repair scheme reinstates load transfer over the entire tendon-to-bone insertion footprint (see e.g., FIG. 6, FIG. 9). This increase in load transfer results in an improvement in overall repair construct mechanical properties, similar to the adhesive-coated suture case disclosed previously (see e.g., U.S. patent application Ser. No. 14/940,541; FIG. 1-FIG. 5). Achieving the full strength of a healthy tendon enthesis may not be necessary, since the enthesis can accommodate higher loads than are applied physiologically during non-traumatic activities. Generation of functional repairs can be capable of sustaining activities of daily living and enhanced rehabilitation protocols.

Here, a shear lag analysis to predict the ability of adhesive interlayers to improve load transfer across a repaired tendon-to-bone enthesis was employed. A finite element model was analyzed with the same geometric and material properties to establish the limits of the scaling law from shear lag analysis for adhesive thickness and adhesive shear modulus. Using these models, desirable adhesive mechanical properties were identified for use in adhesive films for tendon-to-bone repair (see Example 1). Adhesives were then biomechanically tested between tendon and bone planks (see Example 3) and in human cadaver rotator cuff repairs (see Example 4) to validate the models and assess adhesives' potential for clinical usefulness.

As described herein, a similar technique can be used, but a modified suture with a collagen-binding adhesive would be implanted. The adhesive is activated after the suture is sewn into position. Here, the goal is to shift the load from the anchor points to shear along the suture length (see e.g., FIG. 1A-FIG. 1B). This minimizes stress concentrations at the repair site.

Historical focus has been on improving procedure and suture materials, but not suture mechanics or other materials like the adhesive film as described herein. Decades of work improving suture techniques has only led to a few percent improvement in strength. Extrapolation from failure data indicates that even a modest 35-50% improvement in load transfer can reduce repair-site failure by 60%.

Film or Layer

In some embodiments, the present disclosure provides a film or layer for use in a subject with a tissue defect.

In some embodiments, the film or layer can be a biocompatible film or a biocompatible layer. As described herein, a layer can be an adhesive film (aka "sticky film") or adhesive layer. The layer can comprise an adhesive, can be a film comprising an adhesive, or can be an adhesive layer. In some embodiments, the layer or film (e.g., layer of adhesive, an adhesive layer, or a biomaterial film) can have porosity to allow for diffusion of proteins and migration of cells through its thickness. The film can be coated with or the layer can be a bioadhesive material to create the equivalent of double-sided tape for biologic applications. The film or layer can be an adhesive material itself, which can slowly interpenetrate to tissues and crosslinks. The film or adhesive layer can also be formed by an injection of liquid adhesive solutions such as hydrogels or any polymers in an aqueous solution. The film or the layer can be impregnated with a delivery system for the release of growth factors and/or seeded with cells. The film or the layer can be interposed between the tendon and bone and a standard surgical repair can be performed. The film can adhere to tendon on one side and bone on the other side, providing shear resistance and improving the strength of the tendon-to-bone repair. Release of growth factors and/or delivery of stem cells to the repair site can further enhance the repair by enhancing healing of the tendon to the bone. In one suitable embodiment, the film or the layer can be, but is not limited to, a porous biodegradable adhesive film or layer adapted to be interposed between tendon and bone. In some embodiments, a film can be a thin layer. In some embodiments, a coating is layer conforming to a surface. In some embodiments, a film can be a film that is made outside of body before applying it to a tissue. A layer can be an adhesive layer or adhesive film that forms after injecting or secreting a liquid adhesive onto a tissue.

In some embodiments, an adhesive can be applied to the film before or after placement at a damaged tissue site or a tissue to tissue interface.

Figures 6A, 6B:
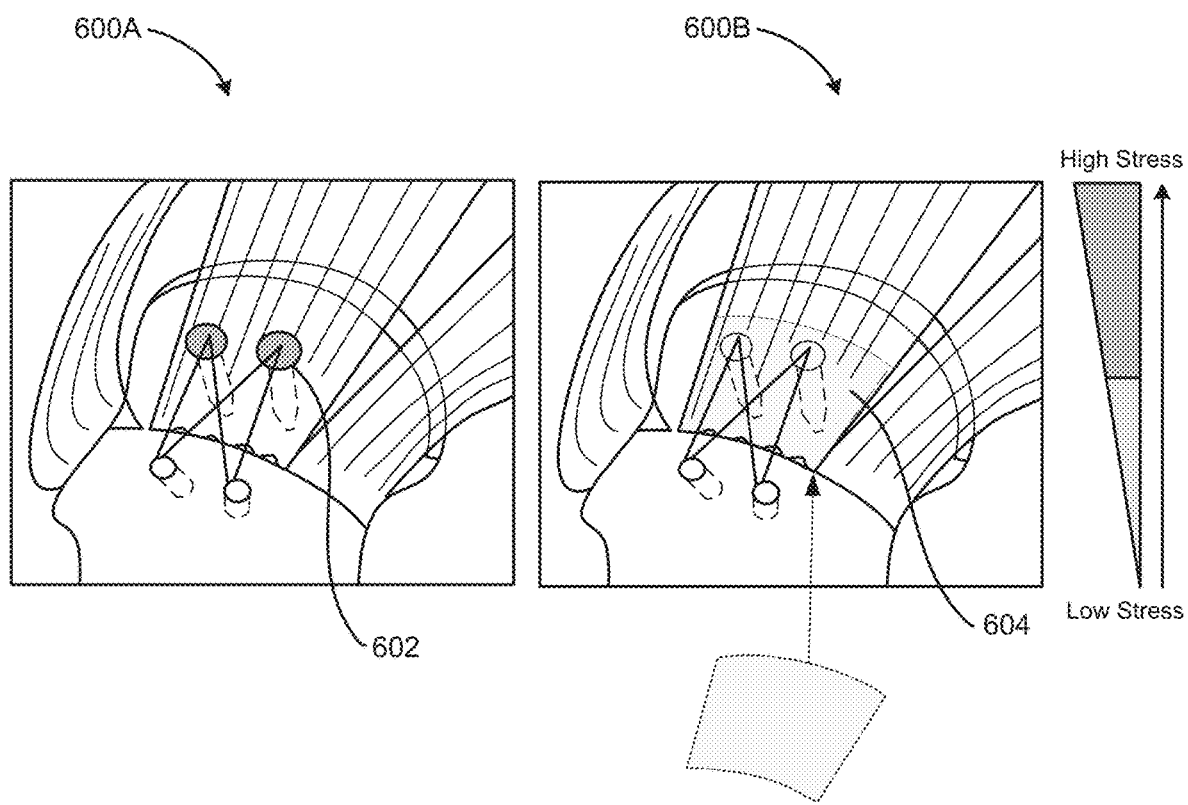
FIGS. 6A-FIG. 6B show approximate stress distributions for standard clinical tendon-to-bone repairs (FIG. 6A) versus repairs augmented with adhesive films or adhesive layers interposed between the tendon and bone, using mechanically optimized, adhesive biomaterials (FIG. 6B). A transosseous-equivalent double-row repair technique is shown for human supraspinatus tendon-to-bone insertion repair as an example surgical tendon-to-bone repair for illustrative purposes. Current repair techniques generate stress concentrations at anchor points where the sutures from bone anchors puncture through the tendon, correlating with tissue failure at those points. Adhesive films or adhesive layers interposed between the tendon and bone distribute load transfer over the entire insertion footprint, similar to native tissue, thereby reducing peak stresses and improving overall repair construct mechanics.
Figure 7A:
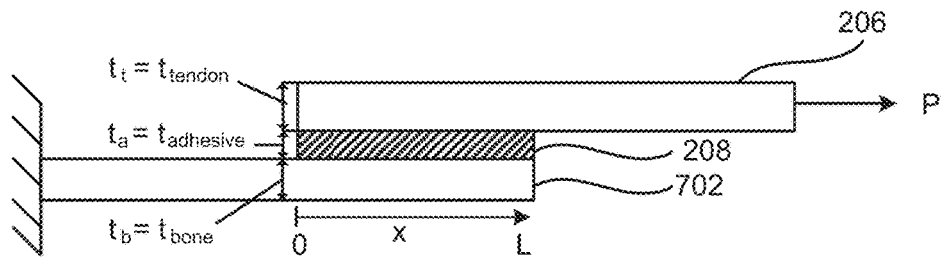
FIG. 7A-FIG. 7C are a series of diagrams of a generic tendon to bone insertion, with an interposed adhesive film or adhesive layer, used to conduct shear lag analysis. P is the tensile load applied to the tendon. Adhesive films or adhesive layers with optimized mechanical properties allow us to maximize this load without repair failure. The tendon is shown in blue, adhesive in brown, and bone in red for illustrative purposes only. The variables represent: t=thickness, E=Young's modulus, G=shear modulus, σ=normal stress, and τ=shear stress at various positions x along the insertion from x=(0, L).
Figure 7B:
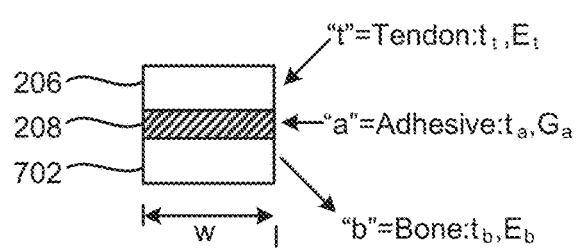
Figure 7C:
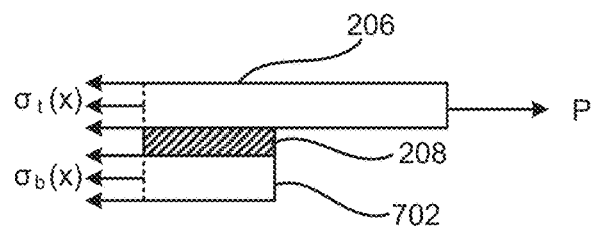
Figure 7D:
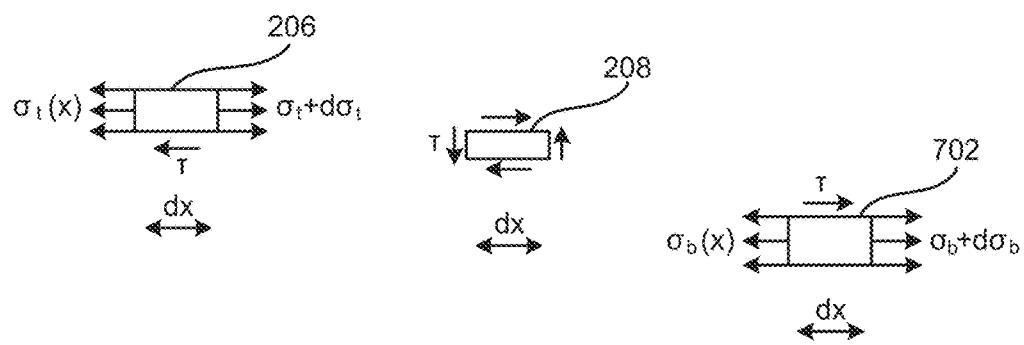
FIG. 7D is a free body diagram (FBD) of differential elements of each component showing tendon 206, adhesive 208, and bone 702.

In some embodiments, the film or layer can distribute loads across the entire tendon-to-bone footprint area rather than solely at the suture-tendon-bone anchor points (see e.g., FIG. 6A-FIG. 6B). This can reduce stress concentrations and provide strengthening and toughening of the attachment in a way that can be optimized by tailoring the film or layer mechanical properties. A further advantage is the delivery of growth factors (GFs) and/or cells, stimulating healing beyond the initial improvement in fixation (see e.g., FIG. 16). The use of the adhesive film or layer in a tendon to bone application was validated using models (see e.g., FIG. 7-FIG. 11); single lap shear tests of idealized sheets of adhered tendon to bone (see e.g., FIG. 12-FIG. 13); and human rotator cuff repairs with tendon adhered to bone (see e.g., FIG. 13-FIG. 14).

The film or layer can comprise a biocompatible film or layer such as a polymer nanofiber mesh, an ionic polymer layer, an ionic polymer film, a biodegradable polyester film, a polysaccharide-based film, a polysaccharide-based hydrogel, a polyester film, or a collagen-based matrix.

Use of a film and films, such as surgical films are well known; see e.g. Schnüriger et al., 2011 Am J Surg 201(1) 111-121. Except as otherwise noted herein, therefore, the process of the present disclosure can be carried out in accordance with such processes.

The film can be a resorbable or degradable polymeric and/or polymeric-ceramic material. As an example, the film can be an anti-adhesion absorbable film (MAST operation American polylactic acid protective film from MAST, Biosurgery Inc.; San Diego, Calif. USA), TephaFLEX® Absorbable Surgical Film, Coaptive film, Cargile Membrane, a preserved peritoneal membrane of the Danish Ox, Interceed, Seprafilm, Adept, Seprafilm, or a pressure-sensitive film.

Adhesive Agent

Processes for defining desirable adhesive properties for adhesives to coat sutures are well known; see e.g. Linderman et al. 2015 Acta Biomat. 23 229-239; and U.S. application Ser. No. 14/940,541, incorporated herein by reference. Except as otherwise noted herein, therefore, the process of the present disclosure can be carried out in accordance with such processes.

Processes for defining desirable adhesive material properties for adhesive films are described herein.

As described herein, the adhesive film or layer can comprise an adhesive. An adhesive can be a biocompatible adhesive, e.g., BioGlue. Biocompatible adhesives have been conventionally used for wound closing and not in tendon/ligament applications. The use has been limited to interface aligned tissues. Adhesives for use in films, as described herein can have properties such as biocompatibility, compatible interfacial and bulk strength, compatible modulus, compatible swelling, and a sufficiently long shelf-life. Adhesive options can include, but are not limited to, catechol-based adhesives, mechanically-based adhesives, bio-glues (e.g., fibrin-based, albumin-based), ionic polymer adhesives, biodegradable polyester adhesives, and polysaccharide-based adhesives. Another adhesive can be a collagen-binding adhesive.

An adhesive agent can be tailored to optimize penetration of the adhesive into soft tissue at a specific depth and nature of penetration. An adhesive can superficially adhere a tissue surface to another tissue surface (e.g., soft tissue or bone) or the adhesive can penetrate a tissue surface into the depth of a tissue.

An adhesive agent can include those defined to penetrate distances ranging from nanometers to millimeters into a fibrous tissue. An optimal range of depth is between one and ten times the mean spacing of fibers.

In some embodiments, the range of depth of adhesive penetration into a soft tissue can be between about 1 nm and about 1 cm.

For example, the adhesive can have a penetration depth of about 1 nm; about 100 nm; about 200 nm; about 300 nm; about 400 nm; about 500 nm; about 600 nm; about 700 nm; about 800 nm; about 900 nm; or about 1000 nm.

As another example, the adhesive can have a penetration depth of about 1 mm; about 100 mm; about 200 mm; about 300 mm; about 400 mm; about 500 mm; about 600 mm; about 700 mm; about 800 mm; about 900 mm; or about 1000 mm.

Recitation of each of these discrete values is understood to include ranges between each value. Recitation of each of a range is understood to include discrete values within the range.

Connective Tissue Growth Factor and Cells

The materials and methods as described herein can comprise a connective tissue growth factor. For example, the growth factor can be CTGF/CCN2.

A growth factor (e.g., CTGF/CCN2) can direct fibroblast differentiation from human mesenchymal stem/stromal cells. A growth factor can be associated with wound healing and fibrosis or heparin binding for sustained release.

CTGF/CCN2 is available from a variety of commercial sources. Preferably, the connective tissue growth factor is human connective tissue growth factor.

Other growth factors that can be used in the methods and compositions as described herein can be a growth factor selected from CTGF, TGFβs (e.g., TGFβ3), CTGF, BMPs (e.g., BMP12), SDF, bFGF, IGF, GDF, PDGF (e.g., PDGF-BB), VEGF, or EGF or their isoforms.

A growth factor can be supplied at, for example, a concentration of about 0 to about 1000 ng/mL. For example, CTGF can be present at a concentration of about 10, about 20, about 30, about 40, about 50, about 60, about 70, about 80, about 90, about 100, about 110, about 120, about 130, about 140, about 150, about 160, about 170, about 180, about 190, about 200, about 250, about 300, about 350, about 400, about 450, about 500, about 550, about 600, about 700, about 750, about 800, about 850, about 900, about 950, or about 1000 ng/mL. For example, CTGF can be present at a concentration of about 100 ng/mL.

A polymers or hydrogel can be a structure to deliver adhesive, growth factor, or cells.

Delivery methods for growth factors include, but are not limited to, hydrogel-based delivery systems, microsphere-based delivery systems and fibrin-based delivery systems. Cells can be seeded directly onto the films for delivery.

As an example, the polymeric delivery system can be a polymeric microsphere, e.g., a PLGA polymeric microspheres. A variety of polymeric delivery systems, as well as methods for encapsulating a molecule such as a growth factor, are known to the art (see e.g., Varde and Pack 2004 Expert Opin Biol Ther 4, 35-51). Polymeric microspheres can be produced using naturally occurring or synthetic polymers and are particulate systems in the size range of 0.1 to 500 μm. Polymeric micelles and polymeromes are polymeric delivery vehicles with similar characteristics to microspheres and can also facilitate encapsulation and matrix integration of the compounds described herein. Fabrication, encapsulation, and stabilization of microspheres for a variety of payloads are within the skill of the art (see e.g., Varde & Pack (2004) Expert Opin. Biol. 4(1) 35-51). The release rate of the microspheres can be tailored by type of polymer, polymer molecular weight, copolymer composition, excipients added to the microsphere formulation, and microsphere size. Polymer materials useful for forming microspheres include PLA, PLGA, PLGA coated with DPPC, DPPC, DSPC, EVAc, gelatin, albumin, chitosan, dextran, DL-PLG, SDLMs, PEG (e.g., ProMaxx), sodium hyaluronate, diketopiperazine derivatives (e.g., Technosphere), calcium phosphate-PEG particles, and/or oligosaccharide derivative DPPG (e.g., Solidose). Encapsulation can be accomplished, for example, using a water/oil single emulsion method, a water-oil-water double emulsion method, or lyophilization. Several commercial encapsulation technologies are available (e.g., ProLease®, Alkerme). Selection of an encapsulation agent can depend on the film or adhesive selected.

As described herein, cells can be delivered to the tissue. A cell can be a living cell, a population of cells, a mesenchymal stromal cell, a tendon-derived stem cell, or an adipose-derived progenitor. The cell can be seeded directly onto the film or the layer. The hydrogel or polymer is a delivery agent for the cell. The hydrogel or polymer is interspersed with the cells. The cell can be delivered by a cell sheet within an adhesive film or layer.

Patterning

As described herein, spatial patterns and combinations of adhesive agents, growth factors, and/or other materials including hydrogels and water can be designed to provide optimized strength, toughness, stiffness, and stress redistribution. One embodiment involves adhesives staggered with non-adhesive agents to arrest propagating cracks within the adhesive layer. Another embodiment involves adhesives randomly interspersed with a non-adhesive hydrogel to reduce the stiffness of the adhesive layer. Another embodiment involves patterning with a non-adhesive hydrogel to create a gradient in adhesion strength along the length of the film. Another embodiment involves adhesives with variable molecular length interspersed to promote adhesion across length scales. Another embodiment involves patterning in thickness of adhesives.

Parameters

As described herein, material (e.g., adhesive) or repair parameters can be optimized according to specific tissue needs.

In some embodiments, the shear modulus ($G_a$) value of a material or repair can be between about $10^3$ and about $10^{10}$ Pa. For example, the shear modulus value can be about $10^3$ Pa, about $10^4$ Pa, about $10^5$ Pa, about $10^6$ Pa, about $10^7$ Pa, about $10^8$ Pa, about $10^9$ Pa, or about $10^{10}$ Pa. Recitation of each of these discrete values is understood to include ranges between each value. Recitation of each of a range is understood to include discrete values within the range.

In some embodiments, the failure shear stress ($\tau_{fail}$) value of a material or repair is between about $10^5$ Pa and about $10^7$ Pa. For example, the failure shear stress ($\tau_{fail}$) value can be about $10^5$ Pa, about $10^6$ Pa, or about $10^7$ Pa. Recitation of each of these discrete values is understood to include ranges between each value. Recitation of each of a range is understood to include discrete values within the range.

In some embodiments, the expected strength improvement from an adhesive film or adhesive layer, calculated based on material and geometric properties of the adhesive and repair, can be between about 3% and about 3000% of the current strength of repairs without adhesive films or adhesive layers. For example, the expected repair strength improvement value can be about 0%; about 100%; about 200%; about 300%; about 400%; 500%; about 600%; about 700%; about 800%; about 900%; about 1000%; about 1100%; about 1200%; about 1300%; about 1400%; about 1500%; about 1600%; about 1700%; about 1800%; about 1900%; about 2000%; about 2100%; about 2200%; about 2300%; about 2400%; about 2500%; about 2600%; about 2700%; about 2800%; about 2900%; or about 3000% of the strength of repairs without adhesive films or adhesive layers. Recitation of each of these discrete values is understood to include ranges between each value. Recitation of each of a range is understood to include discrete values within the range.

In some embodiments, the strength (maximum load (N)) value of a material or repair can be between about 0 N and about 3000 N. For example, the strength (maximum load (N)) value of a material or repair can be about 0 N; about 100 N; about 200 N; about 300 N; about 400 N; 500 N; about 600 N; about 700 N; about 800 N; about 900 N; about 1000 N; about 1100 N; about 1200 N; about 1300 N; about 1400 N; about 1500 N; about 1600 N; about 1700 N; about 1800 N; about 1900 N; about 2000 N; about 2100 N; about 2200 N; about 2300 N; about 2400 N; about 2500 N; about 2600 N; about 2700 N; about 2800 N; about 2900 N; or about 3000 N. Recitation of each of a range is understood to include discrete values within the range. Recitation of each of a range is understood to include discrete values within the range.

In some embodiments, the strength, the toughness, the resilience, or the stiffness of the adhesive or repair will be optimized for the specific damaged tissue.

Formulation

As described herein, an adhesive or agents can be applied to a film and implanted into a subject, directly applied into a subject, or applied to an object such as a suture before being implanted in a subject. Such adhesives or agents can be a formulated adhesive or agent. Also described herein, a scaffold of the present disclosure can be implanted in a subject. Such scaffold can include various pharmaceutically acceptable carriers or excipients.

The agents and compositions described herein can be formulated by any conventional manner using one or more pharmaceutically acceptable carriers or excipients as described in, for example, Remington's Pharmaceutical Sciences (A.R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Md., 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutical active substances is well known in the art (see generally Remington's Pharmaceutical Sciences (A.R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, parenteral, pulmonary, oral, topical, intradermal, intramuscular, intraperitoneal, intravenous, subcutaneous, intranasal, epidural, ophthalmic, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations can also be used to affect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

Therapeutic Methods

Also provided is a process of treating a musculoskeletal injury in a subject in need administration of a therapeutically effective film, so as to improve surgical outcome.

Methods described herein are generally performed on a subject in need thereof. A subject in need of the therapeutic methods described herein can be a subject having, diagnosed with, suspected of having, or at risk for developing a musculoskeletal injury. A determination of the need for treatment will typically be assessed by a history and physical exam consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, hamsters, guinea pigs, and chickens, and humans. For example, the subject can be a human subject.

Generally, a safe and effective amount of film or agent is, for example, that amount that would cause the desired therapeutic effect in a subject while minimizing undesired side effects. In various embodiments, an effective amount of film or agent described herein can substantially inhibit risk for post-surgical injury, slow the progress of post-surgical injury, or limit the development of post-surgical injury.

According to the methods described herein, administration of the film to the subject can be of any surgical method known in the art.

When used in the treatments described herein, a therapeutically effective amount of adhesive or agent (e.g., growth factor) can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to result in an improved surgical outcome.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, 4$^{th}$ ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Treatment in accord with the methods described herein can be performed prior to, concurrent with, or after conventional treatment modalities for a musculoskeletal injury.

An adhesive or agent can be administered to the film or subject simultaneously or sequentially with another agent. An agent or composition can be administered in combination with a film as described herein wherein the film can be a biodegradable, biocompatible polymeric film that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in contact with or in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; or improve shelf life of the product.

Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to a film, layer, or an adhesive. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

Examples

The following non-limiting examples are provided to further illustrate the present disclosure; these are examples of the inventive concepts and should not be used to limit the scope of the claims. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved. Accordingly, the drawings and descriptions should be regarded as illustrative in nature and not restrictive.

Example 1: Modeling to Predict Desirable Adhesive Properties for Rotator Cuff Repair This Example identifies adhesives with desirable properties for tendon-to bone repair using a shear lag model, with the results corroborated by a finite element model. The model predicted load sharing across an idealized tendon-to-bone insertion site using an interposed adhesive layer at the interface. The idealized repaired tendon and bone were both modeled as isotropic, homogenous tissue planks. As an example tendon-to-bone repair, the rotator cuff supraspinatus insertion into the underlying humeral head bone was modeled with an adhesive film interposed between the tendon and bone (FIG. 6).

Figure 8A:
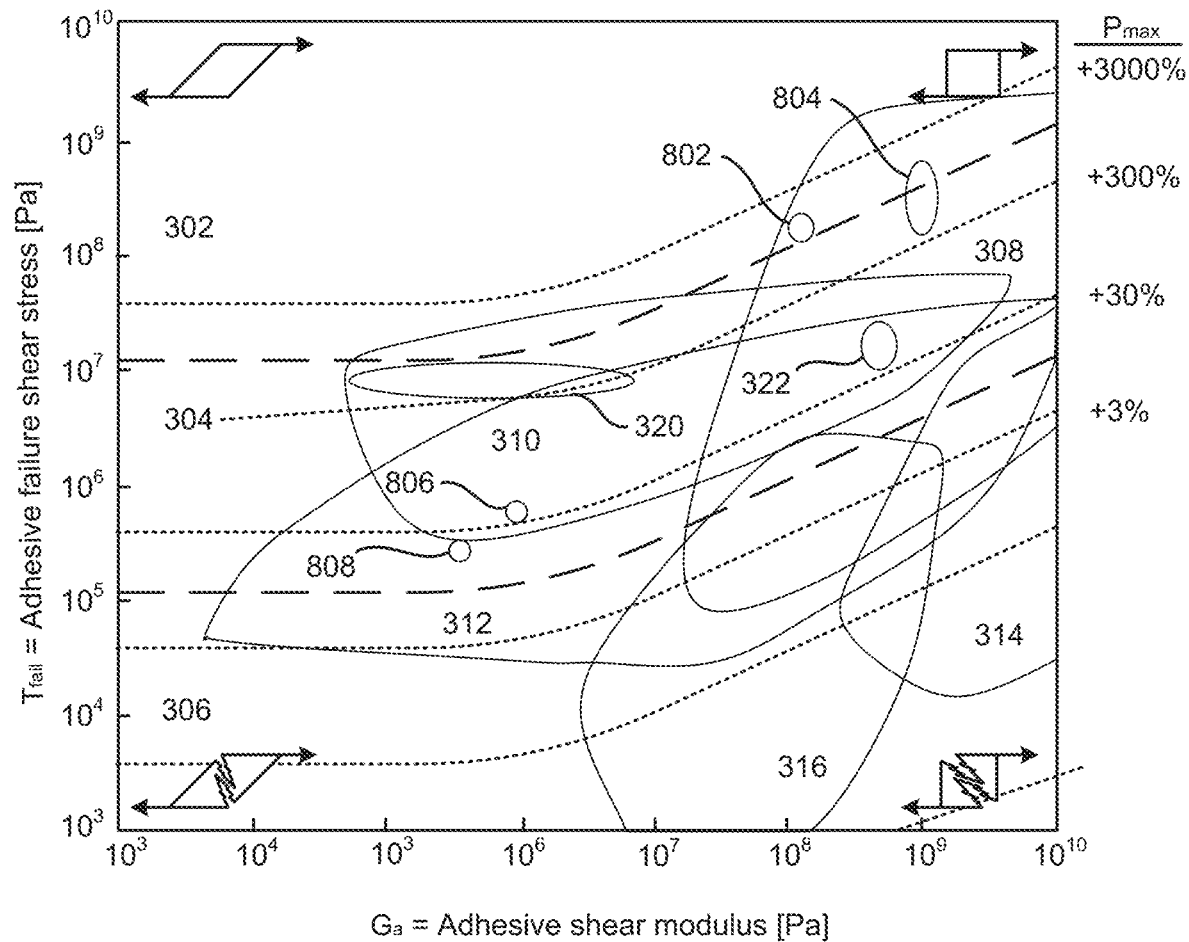
FIG. 8A is a contour map showing the design space for adhesive biomaterials for use in adhesive films or adhesive layers, using the human supraspinatus tendon-to-bone insertion parameters (TABLE 2) as an example of one such repair in order to calculate relevant values. The x-axis shows the shear modulus of the adhesive material, y-axis shows the shear stress at which the adhesive material fails, and the contours show the total maximum force transferred across the repair site via the adhesive as a percentage of the current repair supraspinatus double-row strength (i.e., approximately 350 Newtons or 1.35 megaPascals). This domain map is overlaid with real material properties to highlight promising materials for further adhesive development. As an example adhesive film composition, a repair using an adhesive layer comprised of a cow tendon plank treated with 100 milliMolar tetrakis (hydroxymethyl) phosphonium chloride (THPC), adhered to tendon and bone with a cyanoacrylate at the interfaces, is expected to improve repair strength by approximately 30% or 400 kiloPascals, as validated experimentally. Experimental results indicate that adhesives provide an additive improvement compared to repairs without adhesives. The contour map illustrates areas of repair strength increase limited by suture strength 302, repair strength increase 304, and limited benefit-adhesive fails before current repair 306. Real materials overlaid on the contour map include fibres and particulates 308, elastomers 310, foams 312, ceramics 314, honeycombs 316, styrene butadiene rubber (latex-rubber cement) 318, polychloroprene (Neoprene) 320, flexible Cyanoacrylate 322, spider viscid silk 802, and silkworm silk 804. Cow Tendon (100 mM THPC) 806 and Cow Tendon (0 mM THPC) 808 are also overlaid on the contour map.
Figure 8B:
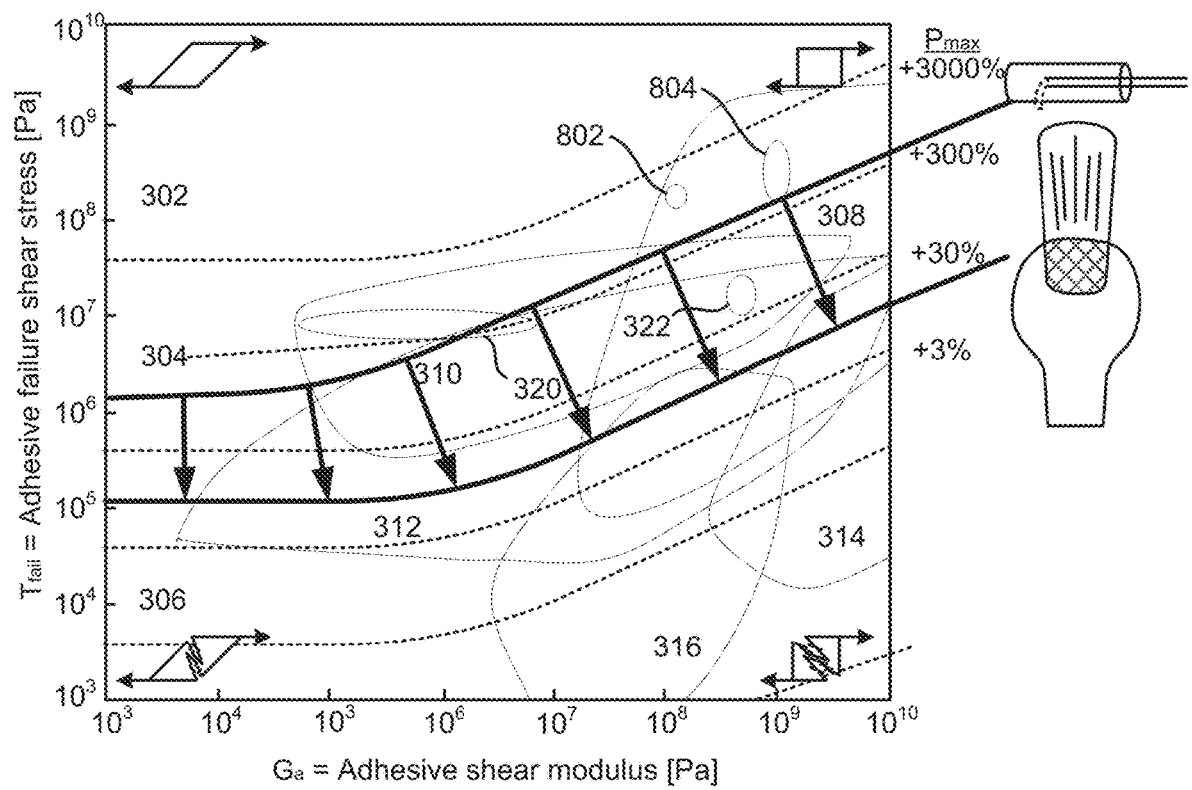
FIG. 8B is a replica of FIG. 8A, overlaid with the contours for adhesive-coated suture (upper solid black line, repeated from FIG. 3) and for adhesive films (lower blue line) showing the lower bounds of the material domains where materials are expected to provide benefit. These contours are based on the two different shear lag models for an adhesive-coated suture within tendon and for an adhesive film interposed between tendon-to-bone, as an example application. This indicates that adhesive films or layers are expected to have many more materials, including the full range of elastomers, provide mechanical benefit for surgical repair compared to adhesive-coated sutures. This is partially due to the increased surface area of adhesive, and partially due to different geometric and material properties for the repair. The contour map illustrates areas of repair strength increase limited by suture strength 302, repair strength increase 304, and limited benefit-adhesive fails before current repair 306. Real materials overlaid on this map include fibres and particulates 308, elastomers 310, foams 312, ceramics 314, honeycombs 316, styrene butadiene rubber (latex-rubber cement) 318, polychloroprene (Neoprene) 320, flexible Cyanoacrylate 322, spider viscid silk 802, and silkworm silk 804.

The shear lag model predicted that mechanically desirable adhesives would be of millimeter-scale thickness and compliant in shear while maintaining high binding and shear strengths. This combination of properties minimizes stress concentration and maximizes load transfer across the repair (FIG. 11 yellow shaded region, and FIG. 8A-FIG. 8B green shaded region). Compliant, thick adhesives allow greater deformation, thereby distributing loads over a larger length than stiff, thin adhesives (FIG. 9, FIG. 10). This is analogous to a native, fibrocartilaginous tendon enthesis, where a compliant zone optimizes stress concentrations and toughens the interface. The derived load transfer isoclines, based on rotator cuff geometric and material properties (TABLE 2), indicate that adhesives with a wide range of theoretical material properties are expected to improve repair strength. When these isoclines are overlaid on real material properties, as in a standard Ashby plot, the model highlights materials with the appropriate properties to improve repair strength (FIG. 8A, region in blue dotted box). Due to the relatively large surface area compared to adhesive-coated sutures (FIG. 3), adhesive films would generate meaningful repair strength improvements using a much broader range of adhesive mechanical properties (FIG. 8B). For example, the entire class of elastomeric materials have appropriate mechanical properties to improve repair strength. Therefore, biocompatible, adhesive elastomeric materials as potential bio-adhesives to improve repair strength have been and are continuing to be explored. Optimal adhesive materials are expected to improve load transfer by over 3,000 N, or 10-fold the strength of a current repair (FIG. 8A).

Shear lag models are one-dimensional, with several limiting assumptions (see the section below on Theory: Shear lag model) that lead to known errors predicting stress distribution around edges and for stiff, thick adhesives on the same thickness order of magnitude as the adherends. Therefore, a finite element model was employed that confirmed that the shear lag model was inaccurate for thick adhesives ($t_a$>1 cm) and stiff adhesives ($G_a$>approximately 1 GPa; FIG. 9). This finite element modeling corroborated the shear lag predictions for adhesives in the desirable range, i.e., compliant, strong adhesives with millimeter-scale or lower thickness. To further refine modeling predictions, other models are envisioned that can incorporate cohesion within the adhesive instead of assuming catastrophic failure, especially to predict sensitivity to flaws in the adhesive material. Nevertheless, the current model provides sufficient predictions of load transfer to guide adhesive material development.

Theory: Shear Lag Model of Adhesive Films for Tendon-to-Bone Repair

As an example tendon-to-bone repair, the rotator cuff supraspinatus tendon insertion into the underlying humeral head bone (see FIG. 6) can be modeled as a single lap shear problem (FIG. 7). Adhesive films with optimized mechanical properties can improve load transfer across repair sites by distributing stresses over a larger area.

The shear lag model studied herein was first derived in classical mechanics literature by Volkersen in 1938, Cox in 1952, and similar to the cylindrical derivation by Linderman et al., *Acta Biomaterialia* 2015. In this context, the shear lag model presented here is representative of the entire class of solid mechanics models used to predict stress fields and load transfer, and is useful for: (i) predicting desirable adhesive properties for tendon-to-bone repair and (ii) anticipating load transfer in idealized experiments to assess adhesive properties. The model is based upon the free body diagram in FIG. 7 and the following assumptions: (i) the tendon, adhesive, and bone are linear elastic materials, (ii) viscous effects are negligible, and (iii) thickness-axis displacements, strains, and stresses are small. The latter assumption is appropriate for thin adhesive layers. These results are also corroborated by 2-dimensional finite element modeling with different assumptions, as described in the following section (Finite element model). While adhesives and tissues often exhibit nonlinearity and viscoelasticity, the linear analysis is adequate and useful for order-of-magnitude stress estimates, and for the target design range in which the adhesive is not close to failure.

As derived by Volkersen directly from equilibrium, constitutive, and strain-displacement equations for the components (i.e., tendon, adhesive, and bone, FIG. 7), the differential equation governing the normal stress in the tendon at position x is:

$$\frac{d^2 \bar{\sigma}_t(x)}{dx^2} - \beta^2 \bar{\sigma}_t(x) + \frac{\beta^2}{\chi} = 0 \tag{3.1}$$

where $\bar{\sigma}_t(x)$ is normal stress in the tendon normalized by the stress, $P/wt_t$ at x=L, and X, and the characteristic (inverse) length scale $\beta$ relate to the geometry and material properties:

$$\chi = \frac{E_b t_b}{E_t t_t} + 1 = \frac{1}{E_t^* t_t^*} + 1 \tag{3.2}$$

$$\beta^2 = \frac{G_a}{t_a}\left(\frac{1}{E_t t_t} + \frac{1}{E_b t_b}\right) = \frac{1}{t_b^2}\frac{G_a^*}{t_a^*}\left(\frac{1}{E_t^* t_t^*} + 1\right) \tag{3.3}$$

where $E_t^*$ and $G_a^*$ are, respectively, the Young's modulus of tendon and the shear modulus of adhesive normalized by the Young's modulus of bone $E_b$; and $t_t^*$ and $t_a^*$ are, respectively, the thickness of the tendon and the thickness of the adhesive normalized by the thickness of the bone cortical layer $t_b$. Solving and applying the boundary condition $\bar{\sigma}_t(0)=0$ at the distal end of the insertion footprint and $\bar{\sigma}_t(L)=1$ at the proximal end of the insertion footprint yields (Equation 3.4, see FIG. 10A):

$$\bar{\sigma}_t(x) = \frac{1 - \cosh(\beta x)}{\chi} + \frac{\sinh(\beta x)}{\sinh(\beta L)}\left(1 + \frac{\cosh(\beta L) - 1}{\chi}\right) \tag{3.4}$$

Combining Equation 3.4 with the equilibrium equation for an infinitesimal segment of tendon yields the following expression for shear stress $\tau(x)$ as a function of position x, normalized by the average shear stress $$\tau_{ave} = \frac{P}{wL},$$

as predicted by Volkersen (see FIG. 9A):

$$\frac{\tau(x)}{\tau_{ave}} = \frac{\beta L}{\chi \sinh(\beta L)}[\cosh(\beta(L-x)) + (\chi - 1)\cosh(\beta x)] \tag{3.5}$$

TABLE 2

Property values used throughout modeling and testing for shear lag analysis (SLA), finite element modeling (FEM), idealized tendon-to-bone plank tests, and human cadaver supraspinatus repair tests.

| | | SLA | FEM | Plank tests | Human |
|---|---|---|---|---|---|
| | Geometric properties | | | | |
| L | adhesive lap length i.e., supraspinatus tendon insertion size (medial-lateral) | 13 mm | 13 mm | 10 mm | 13 mm |
| $L_{b,free}$ | free length of bone plank before grip | — | 26 mm | 5 mm | — |
| $L_{t,free}$ | free length of tendon plank before grip | — | 26 mm | 25 mm | — |
| w | lap width i.e., supraspinatus tendon insertion size (anterior-posterior) | ∞ | ∞ | 15 mm | 20 mm |
| $t_t$ | tendon thickness | 2 mm | 2 mm | 3.2 mm | 2 mm |
| $t_a$ | adhesive thickness | [1 nm-1 cm] | [1 μm-1 cm] | ≈0.5 mm | ≈0.5 mm |
| $t_b$ | bone cortical shell thickness | 7.5 mm | 7.5 mm | 7.5 mm | 7.5 mm |
| | Mechanical properties | | | | |
| P | force applied to tendon to model shear and normal stresses | 50N | 50N | to failure | — |
| $E_t$ | tendon elastic modulus | $2 \cdot 10^8$ Pa | $2 \cdot 10^8$ Pa | — | — |
| $E_b$ | bone elastic modulus | $2 \cdot 10^{10}$ Pa | $2 \cdot 10^{10}$ Pa | — | — |
| $G_a$ | adhesive shear modulus | $[10^4 - 10^{11}$ Pa] | $[10^4 - 10^{11}$ Pa] | — | — |
| $E_a$ | adhesive elastic modulus | — | $2G_a(1 + \nu_a)$ | — | — |
| $\nu_t$ | tendon Poisson's ratio | — | 0.2 | — | — |
| $\nu_a$ | adhesive Poisson's ratio | — | 0.49 | — | — |
| $\nu_b$ | bone Poisson's ratio | — | 0.3 | — | — |
| $\tau_{fail}$ | adhesive shear ultimate strength | $[10^4 - 10^{10}$ Pa] | — | — | — |

This shear lag model predicts that shear stress is highest at the edges of the lap joint, i.e., at positions x=0 and x=L, and that shear stress decreases exponentially toward more central positions (Equation 3.5). Note that as previously demonstrated for lap joints, parametric analysis of Equation 3.5 confirmed that peak stress is minimized if the adherends (tendon and bone) are "balanced" so that $E_t^* = (t_t^*)^{-1}$. However, this is not the case for the tendon-to-bone attachment. Indeed, the material mismatch at a tendon-to-bone attachment leads to stress concentrations and makes surgical repair particularly challenging. For the geometric and material properties of a tendon-to-bone repair (TABLE 2), the peak shear stress occurs at position x=L (3.5). Thus, evaluating Equation 3.5 at position x=L describes the stress concentration factor $\tau_{SCF}$ (see FIG. 11):

$$T_{SCF} = \frac{\tau}{\tau_{ave}}\bigg|_{x=L} = \frac{(\beta L)}{\chi \sinh(\beta L)}[1 + (\chi - 1)\cosh(\beta L)] \quad (3.6)$$

Equating the peak shear stress (at position x=L) to the failure shear stress value, $\tau_{fail}$, yields the maximum load transferred across the joint via the adhesive:

$$\left(\frac{P_{max}}{w}\right) = \tau_{fail} L \frac{\sinh(\beta L)}{\beta L}\left[\frac{\chi}{(\chi - 1)\cosh(\beta L) + 1}\right] \quad (3.7)$$

This is used to generate the contour map design space shown in (FIG. 8), which is then overlaid with real material properties to highlight desirable materials from which to develop adhesive biomaterial films. This derivation uses supraspinatus tendon insertions as an example to calculate values, but it is relevant for surgical attachments throughout the body.

This scaling law for maximum load transfer enabled prediction of desirable adhesive mechanical properties for surgical use in tendon-to-bone repairs (FIG. 8A). The shear lag model theory herein is applicable to tendon- or ligament-to-bone repairs generally, by simply updating the properties in (TABLE 2) according to the soft tissue-to-bone insertion site of interest. Note that fail could be limited by failure (i) within the adhesive bulk, (ii) at the interfaces with adherends (i.e., the junction with the tendon or bone), or (iii) within the adherends themselves. This solution is nearly bilinear, with two asymptotes (FIG. 8A):

$$\lim_{G_a \to 0}\left(\frac{P_{max}}{w}\right) = \lim_{\beta \to 0}\left(\frac{P_{max}}{w}\right) = \tau_{fail} L \quad (3.8)$$

$$\lim_{L \to \infty}\left(\frac{P_{max}}{w}\right) = \tau_{fail}\frac{\chi}{\beta(\chi - 1)} \quad \tau_{fail} t_b^2 t_t^* t_a^* \frac{E_t^*}{G_a^*} \quad (3.9)$$

Note that the asymptote described by Equation 3.9 is not dependent on any bone material or geometric properties, since peak shear stress occurs at position (x=L) for the property values of a supraspinatus tendon repair.

In a theoretical situation in which the adherends were unbalanced in the opposite direction, so the peak shear stress occurred at position (x=0), the maximum force transferred would be:

$$\left(\frac{P_{max}}{w}\right)\bigg|_{opposite\ inbalance} = \tau_{fail} L \frac{\sinh(\beta L)}{\beta L}\left[\frac{\chi}{\cosh(\beta L) + (\chi - 1)}\right] \quad (3.10)$$

Similar to Equation 3.7, this is a nearly bilinear solution with asymptotes given by Equation 3.8 and:

$$\lim_{L \to \infty}\left(\frac{P_{max}}{w}\right)\bigg|_{opposite\ inbalance} = \tau_{fail}\frac{\chi}{\beta} = \tau_{fail} t_b^2 t_a^* \frac{1}{G_a^*} \quad (3.11)$$

In this theoretical situation, the asymptote given by Equation 3.11 is independent of tendon properties.

Shear Lag Model Limitations:

The shear lag model employed herein is one dimensional and ignores loads that are not directly in line with the tendon (considered isotropic, linear elastic herein). This is a major simplification of the rotator cuff, where the high degrees of freedom during rotation and other movements would apply multi-dimensional load to the supraspinatus attachment. However, (i) the majority of that load will be carried by other muscles and ligaments and (ii) the adhesive and repair are able to withstand some load in off-axis directions.

The shear strength used in the shear lag modeling to predict load tolerance was the failure shear stress $\tau_{fail}$ at the local, material level. The shear stress measured in idealized plank tests was averaged over the interface ($\tau_{ave}$). The optical tracking performed in the experiments used semi-local strain determination, which is more relevant than grip-to-grip strain measurements since it does not include the strain-energy stored in tissues outside the repair site. However, this analysis did not include a local strain assessment to determine the peak shear stress within the adhesive layer. Such local assessments have been effectively used for tracking strains and detecting cracks forming in biological tissues; however, they are difficult to measure in thin adhesive layers due to insufficient number of pixels. Regardless, they are largely unnecessary for determining adhesive efficacy.

Theory: Finite Element Model of Adhesive Films for Tendon-to-Bone Repair

In order to establish the limits of the scaling law described in the previous section (Shear lag model), a two-dimensional finite element model was evaluated in the commercial package COMSOL. This finite element model was created with the same geometric and material properties as the shear lag model (TABLE 2). The tendon, adhesive, and bone were modeled as linear elastic materials. There were 8,000 finite elements in the adhesive layer, sized from 1-50 μm, with more dense element meshing closer to the edges. The interfaces between adhesive and tendon or bone were modeled as perfectly fused unions, joined at all nodes of the boundary along which the sections abut. Far from the adhesive joint, the bone was fixed from movement or rotation in the x or y directions. The tendon was allowed to move in the x direction but not allowed to rotate or move in the y direction, and a distributed load totaling 50 N was applied uniformly over the x direction to simulate muscular contraction applying force to the tendon (TABLE 2).

Results of Shear Lag and Finite Element Modeling

Figure 11:
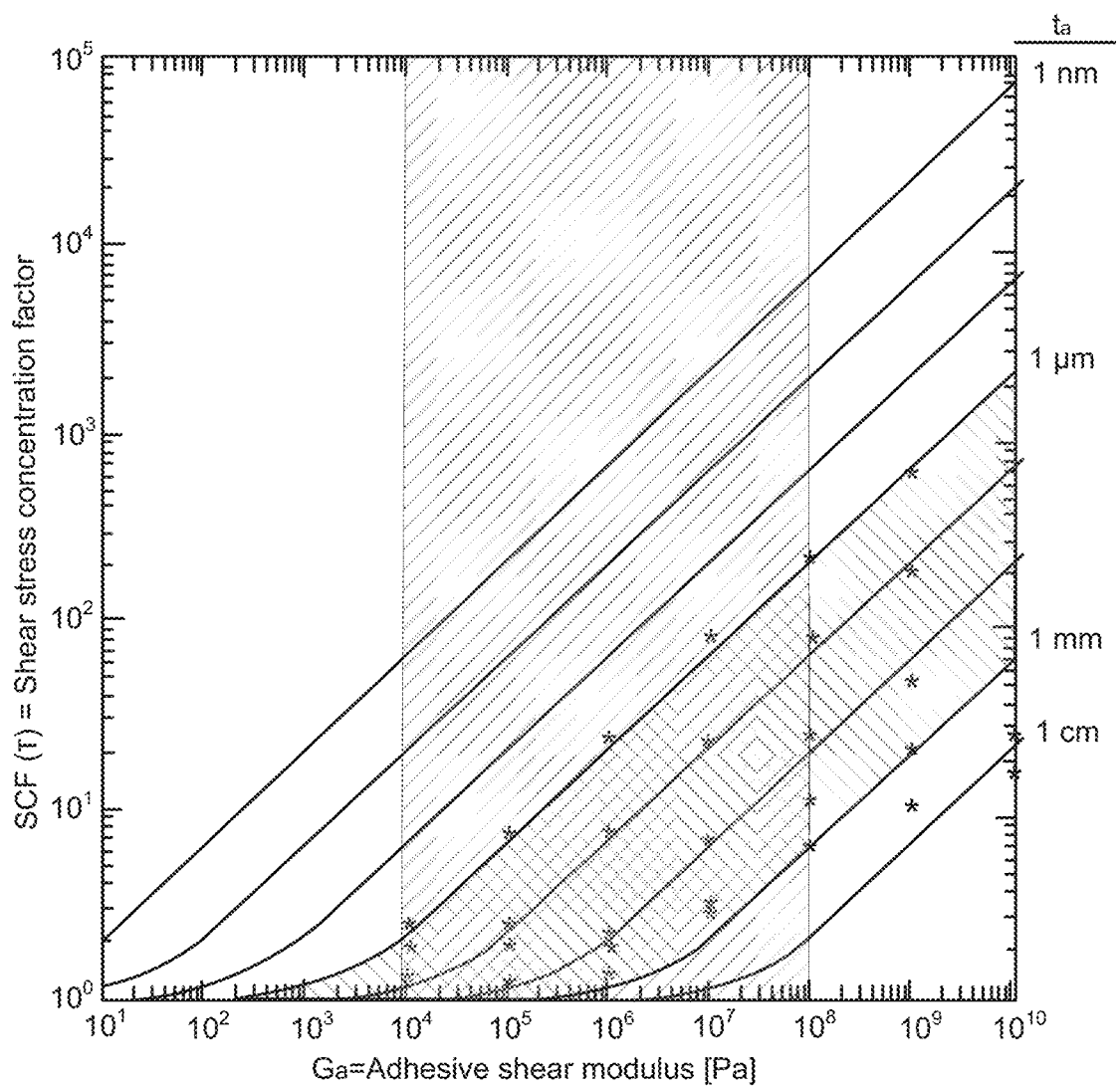
FIG. 11 is a graph showing that the shear lag modeling predicted the lowest stress concentration for compliant, thick adhesives. The solid lines are calculated solely based on shear lag modeling of an adhesive film or adhesive layer interposed in a tendon-to-bone repair. The asterisks are calculated based on finite element modeling. Line or asterisk color represents thickness of the adhesive layer (labeled on right). Hatched, shaded regions highlight the relevant ranges of adhesive shear modulus ($G_a=10^4$-$10^8$ Pascals) and adhesive thickness ($t_a=1$ micrometer-1 millimeter), with the overlapping relevant range highlighted in yellow. The shear lag modeling closely matched finite element modeling for adhesive thickness below 1 millimeter.
Figure 13A:
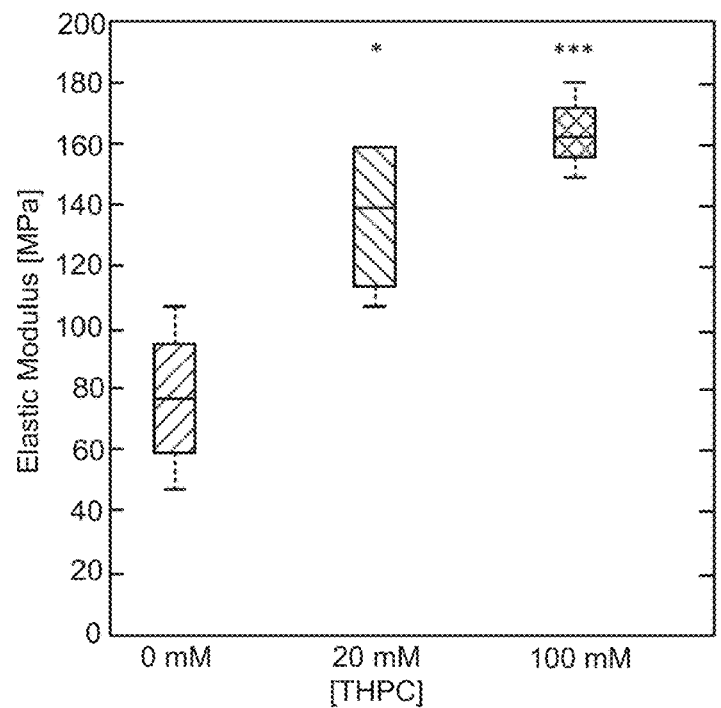
FIG. 13A-FIG. 13D are a series of box plots demonstrating mechanical testing results, tested as shown in FIG. 12.
Figure 13B:
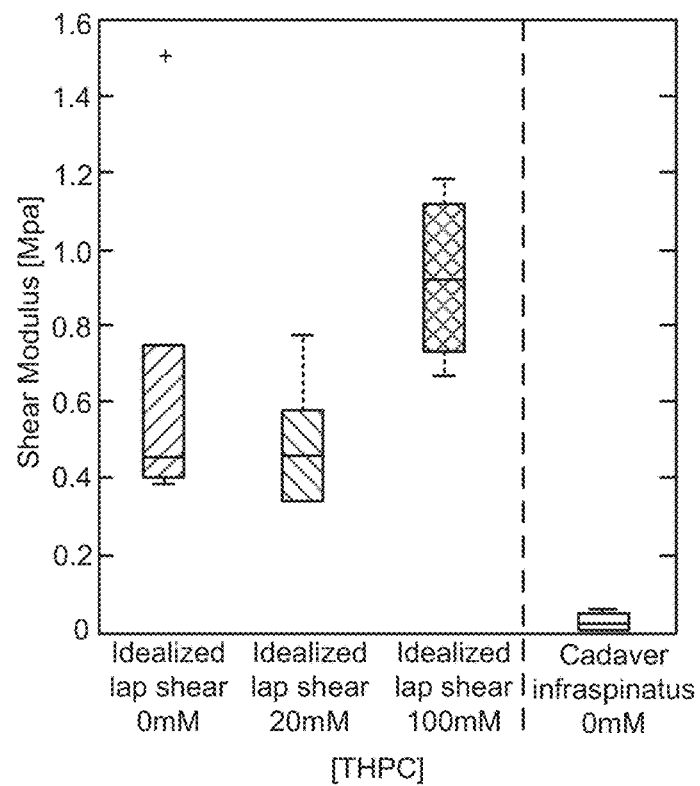
Figure 13C:
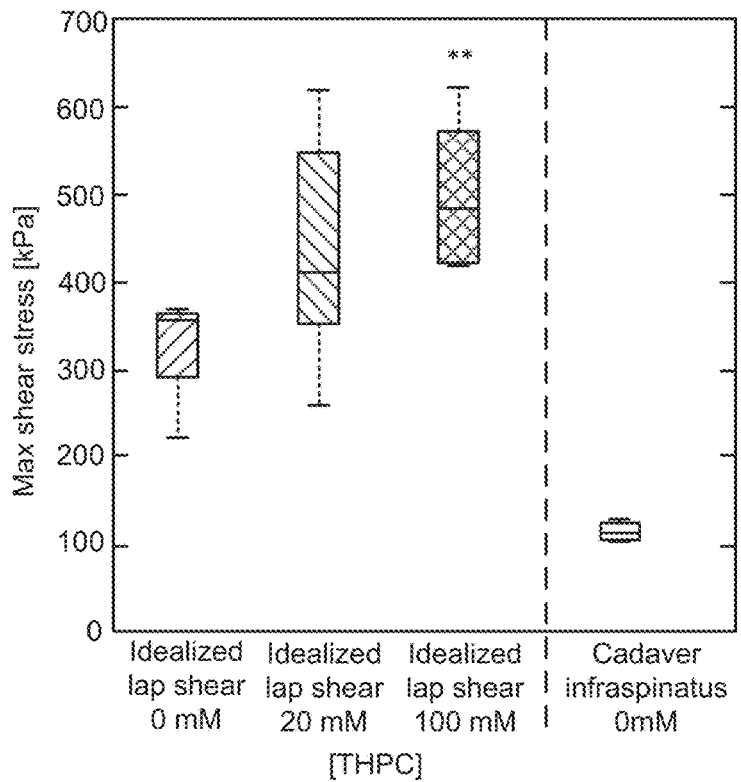
Figure 13D:
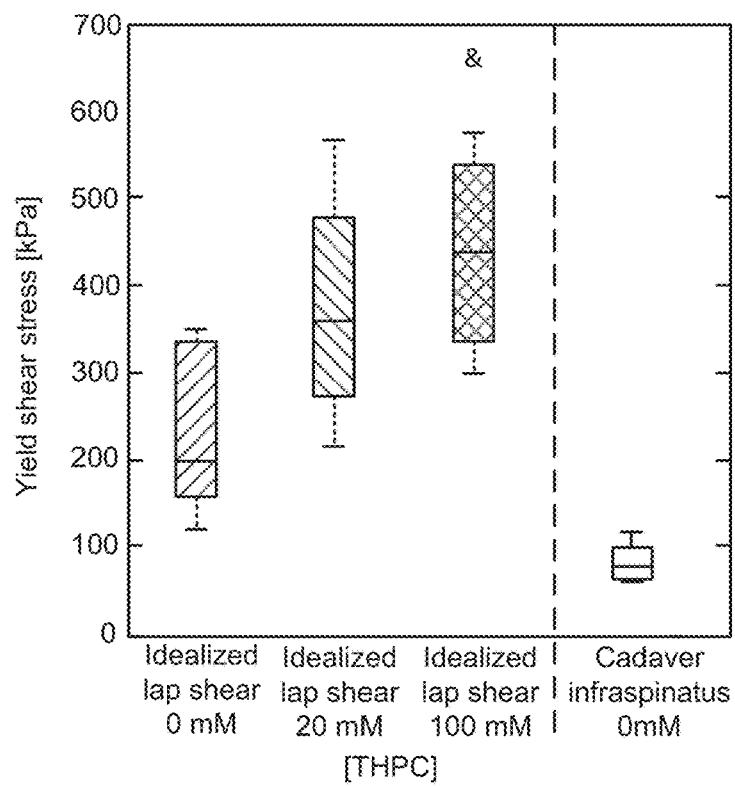

Shear lag and finite element modeling revealed an ideal design space for adhesive mechanical properties to improve load transfer across tendon-to-bone repairs (FIG. 8A, band inside blue dotted box, including the elastomer material class). As with adhesive-coatings on sutures (see FIG. 3), mechanically desirable adhesives should be compliant in shear while maintaining high binding and shear strengths. Higher deformation of compliant adhesives facilitates load distribution over larger lengths than stiff adhesives, reducing the peak stress (FIG. 9, FIG. 10). Similarly, thick adhesives allow higher deformation than thin adhesives, reducing the shear stress concentration factor. Shear lag analysis predicted stress concentration factors of approximately 1-200 for the experimentally relevant ranges of adhesive shear modulus and thickness ($G_a=10^4$-$10^8$ Pa and $t_a$=1 μm-1 mm, respectively) (FIG. 11).

While shear lag analyses generate simple, closed form solutions, the simplifying assumptions described in the Theory section (shear lag model) lead to inaccurate stress predictions at edges (x=0 and x=L) and in cases of stiff or thick adhesives layers. The finite element predictions of normal stress distribution in the tendon and shear stress distribution in the adhesive (FIG. 10B and FIG. 9B, respectively) closely resembled the shear lag predictions for compliant adhesive layers (FIG. 10A and FIG. 9A), but deviated for adhesive shear moduli greater than ~$10^8$-$10^9$ Pa. However, the predicted peak shear stress (i.e., at position x=L for shear lag predictions, slightly in from position x=L for finite element predictions) remained similar for the two models even for $G_a$>$10^8$ Pa, and only substantially deviated for $G_a$ $10^{10}$ Pa. The finite element model corroborated the shear stress concentration factor predictions from shear lag analysis for adhesives up to 1 mm thick (FIG. 11).

A contour map of maximum load transfer given various adhesive properties was generated from Equation 3.7 using an adhesive thickness of 0.5 mm (FIG. 35). Properties of several real materials were then overlaid on this contour map to identify promising candidate materials. Only a small fraction of the material classes shown are relevant materials; the remainder are included for comparison as is standard with an Ashby plot, and to highlight the importance of appropriate adhesive material selection. Assuming a compliant adhesive (Ga=1 MPa) with a shear strength r on the order of about 10 MPa and assuming the average adult supraspinatus tendon insertion geometric properties (TABLE 2), maximum load transfer through would approach 3,000 N of force. This would result in theoretical improvements of up to approximately 10-fold over current methods using a double row suture anchor repair, causing repair strength to be limited by tissue strength.

The maximum load transfer prediction herein uses supraspinatus tendon insertions as an example to calculate values, but it is relevant for surgical attachments throughout the body.

Example 2: Tissue to Bone Adhesive Film

The following example describes the development of adhesive biomaterials to improve load distribution of repairs, evaluation of biocompatibility, and assessment of surgical outcomes in large animals. The film shifts the load from a few anchor points to shear along the entire adhesive sheet which minimizes stress concentrations at the repair site.

Development of Adhesive Biomaterials

Adhesive biomaterials distribute stress and improve load transfer. Interfacial binding to tendon can be achieved through factors such as the following:

NHS-ester chemistry
Enzymatic reaction: Transglutaminase
Peptide based binding—QCM (Initial results are not promising)
Acrylates
Enzymatic reaction: Peroxidase+$H_2O_2$
Catechol/dopa chemistry
"Tissue welding"

A specific NHS chemistry is the following.

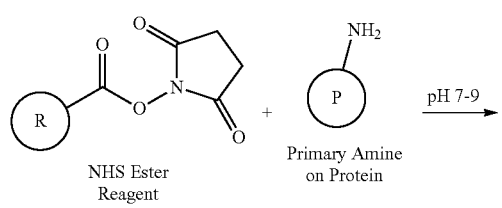

NHS Ester Reagent + Primary Amine on Protein → pH 7-9

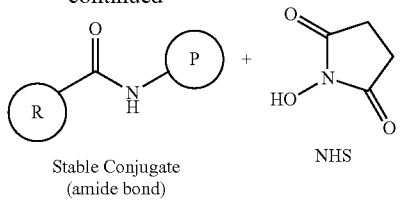

Stable Conjugate (amide bond) + NHS

Amine specific binding works in slightly basic conditions, binds the N-terminus of peptide, and Lysine ε-amine. Lysine's ε-amine group has pKa around 10.5. Note that SDP esters are significantly less susceptible to hydrolysis than succinimidyl esters and TFP esters. This often needs a hydrophobic solvent, such as DMF or DMSO. The spacer arm 5-35 Angstroms.

Activatable Protective Layers

A fatty-acid based phase change material (PCM) can be applied as protective coating on adhesive coated sutures. This can provide for a tunable melting temperature. Agent can be encapsulated to activate the adhesive binding to tissue (e.g., lysyl oxidase, HRP).

Evaluation of Biocompatibility

In vitro cell responses to adhesive materials were checked. Co-culture of biomaterial components with primary tendon fibroblasts (mouse tendons) was used. Outcomes of cell survival, proliferation, death, inflammation, and matrix synthesis were checked.

Assessment of Surgical Outcomes

Assessment of surgical outcomes was also performed following canine flexor digitorum profundus tendon tenotomy and repair. Biomechanics and biochemistry were performed at 28 days on 8 repairs, and gene expression and histology at 7 days and 28 days were performed on 6 repairs. It was concluded that adhesive-coated sutures can improve load transfer, and that improved load transfer can decrease rupture rate.

Example 3: Idealized Ex Vivo Tendon-to-Bone Plank Tests

Experimental Methods Section

New Lap Shear Testing Method:

Lap shear tests are a standard method to determine adhesive mechanical properties for engineering applications; however, the applications described herein require binding to biological tissues instead of metal or plastic adherends. In order to evaluate adhesive properties with relevant adherends and assess adhesive usefulness for tendon-to-bone repair, a new method for lap shear testing using tendon and bone planks was developed (FIGS. 12A-12B). Tendon plank fabrication using a sliding microtome and a sacrificial teflon piece to measure thickness enabled creation of highly uniform, geometrically standardized planks. Pilot experiments demonstrated that tendons needed to be planed on both sides and curved edges removed to create the desired width of 15 mm for testing. Otherwise, the curvature in the tendon samples created a non-uniform thickness that amplified stresses in some parts of the tendons. Similarly, bone planks were created using a diamond blade to create precisely-sized samples. This protocol enabled rapid testing of adhesive properties via lap shear with relevant adherends for clinical application. This standardized testing setup allowed accurate characterization of adhesive properties before surgical use. Note that the failure shear strength, $\tau_{fail}$, used in the shear lag model can be limited by: (i) the bulk adhesive strength (cohesion), (ii) the interfacial binding strength to the surrounding tissue, and/or (iii) the ability of the surrounding tissue to accommodate load transfer (e.g., through distributing shear stress among tendon fibers). Since the adherends are relevant to the repair setting, the failure shear stress measured in these lap shear experiments is reflective of the failure shear stress of the adhesive.

A series of idealized tendon-to-bone plank repairs was performed using ⅛" thick bovine deep digital flexor tendon planks adhered to ¼" thick bovine femur cortical bone planks (both planks were 15 mm wide, with 10 mm overlap length; TABLE 2). Fresh-frozen bovine deep digital flexor tendons (age 14-30 months; Animal Technologies, Tyler, Tex.) were leveled into planks while embedded in Tissue-Plus optimum cutting temperature compound (OCT, Fisher HealthCare, Waltham, Mass.) using a freezing stage (BFS-30MP, Physitemp, Clifton, N.J.) sledge microtome (Leica 1400, Buffalo Grove, Ill.) to plane both sides to a uniform, desired thickness. The desired thickness was measured using a sacrificial layer of polytetrafluoroethylene (PFTE, commonly called "teflon", McMaster-Carr, Elmhurst, Ill.) on the microtome alongside the tendon samples. After being leveled into planks, samples were frozen in PBS-soaked gauze and stored at −20° C. Samples were thawed overnight at 4° C. and trimmed to 15 mm wide with a razor blade before use. The width was chosen based on the size of bovine deep digital flexor tendons, and to maintain a high width-to-thickness aspect ratio ~5:1. Pilot experiments performed on tendon samples planed on only one side had high variability in shear strength, likely due to variable tissue curvature, necessitating planing samples on both sides. Fresh-frozen bovine femurs obtained from a local butcher were cut into bone planks using a diamond wafer blade (IsoMet, Buehler, Lake Bluff, Ill.). In addition, to rapidly assess adhesive mechanical properties with relevant adherends for use in either tendon-to-bone repair or on adhesive-coated sutures, a series of idealized tendon-to-tendon plank repairs were performed using two ⅛" thick bovine deep digital flexor tendon planks but no bone planks.

Effects of Adhesive Stiffness:

To experimentally assess the impact of varying adhesive stiffness without modifying interfacial binding strength, a series of multipartite adhesive systems was evaluated. Each multipartite adhesive consisted of a 1/16" thick bovine tendon to provide a compliant bulk, attached to the adjacent tendon and bone using 50 µL of a flexible cyanoacrylate on each interface (Loctite 4903, based on ethyl and octyl cyanoacrylate; Henkel Corporation, Dusseldorf, Germany) to provide the necessary bond strength. The 1/16" thick tendon bulk was first treated with PBS containing 0 mM, 20 mM, or 100 mM tetrakis (hydroxymethyl) phosphonium chloride (THPC, Sigma Aldrich, St. Louis, Mo.) for 15 minutes to assess the impact of a two-fold stronger adhesive bulk material (n=6 each). After treatment with THPC, the 1/16" tendon bulk was washed twice in excess PBS (40 mL) on a rocker for 5 minutes before use in the multipartite adhesive system. (THPC covalently crosslinks amine groups in proteins) Two tendon plank samples in this experimental series were discarded because the samples were discolored and dramatically stiffer than the other samples, likely due to dehydration and oxidation at some point during the tendon plank processing (a.k.a., "freezer burn"). There were at least n=5 samples in each final group. The adherends and the 1/16" thick tendon bulk pieces were blotted dry with Kimwipes (Kimberly-Clark Professional, Roswell, Ga.) three times before applying cyanoacrylate. This was cured for 3 hours at room temperature under 100 kPa compressive pressure, wrapped in PBS-soaked gauze, before lap shear testing.

In addition to evaluating the multipartite adhesive directly, the elastic modulus of tendon planks treated with THPC was determined by direct tensile testing. A series of ⅛" thick tendon planks, treated with PBS containing 0 mM, 20 mM, or 100 mM THPC for 15 minutes before two washes in PBS, was mechanically evaluated (n=4 each). Two samples were discarded due to discoloration and stiffness before testing, leaving at least n=3 samples per group.

Catechol-Derived Adhesives:

Given the advances in arthroscopic surgical repairs over the last two decades, any adhesive applied to a tendon-to-bone repair will need to function in an underwater environment. In collaboration with Professor Koilbe Ahn at the University of California in Santa Barbara, a series of marine mussel mimetic, catechol-derived adhesive polymers in the idealized tendon-bone and tendon-tendon plank single lap shear model were tested. These polymers are high molecular weight and elastomeric, with catechol-derived chemical binding groups. After thawing the ⅛" thick tendon samples at 4° C. overnight, then trimming them to 15 mm wide and 60 mm long, 100 µL of high molecular weight adhesive homopolymer (no crosslinking polymer) or heteropolymer (including a crosslinking polymer for bulk shear strength upon curing) was applied to a 15 mm wide by 10 mm long tendon plank segment on each plank, all while fully submerged in PBS at pH 7.4. In a different group of samples, the polymer was applied to a wet but not submerged tendon to avoid polymer dissipation in the fluid bath during application. After waiting 30 seconds for partial gelation and phase change, the samples were pressed together under a 100 kPa compressive pressure and re-submerged in PBS, as described above. Samples were cured in PBS either overnight at 4° C., or over 72 hours at 37° C. to induce oxidation and stronger binding, before biomechanical testing.

Biomechanical Testing:

Idealized tendon-tendon and tendon-bone plank repairs were tested similar to previously described protocols for testing flexor tendons. After 5 cycles of triangular-ramp preconditioning to 1 mm displacement, samples were pulled in uniaxial tension using a material testing machine (5866; Instron Corp., Norwood, Mass., chosen because of a high capacity load cell) at 0.3 mm/s until failure. Video of the test was recorded for optical strain tracking. Immediately prior to testing, tendons were stained with a speckle pattern of freshly prepared VerHoeff stain to provide a surface texture for optical tracking. Elongation measurements from the material testing machine were synced with optical recordings from a high resolution camera at a frame rate of 30 Hz (Google *Nexus* 6p, Mountain View, Calif.), similar to described previously. Optical tracking of points on the tendon and bone immediately surrounding the interface enabled accurate determination of semi-local tissue strain. This allowed for more accurate adhesive material property assessment, without confounding the viscoelastic effects or strain-energy storage of the tendon plank proximal to the interface. From the force-elongation curves, maximum force and yield force were determined. From the force-strain curves, strain at 20 N force (approximating strains at physiologically relevant load levels), modulus (slope of the linear portion), and resilience (area under the curve until yield) were determined.

Figure 15:
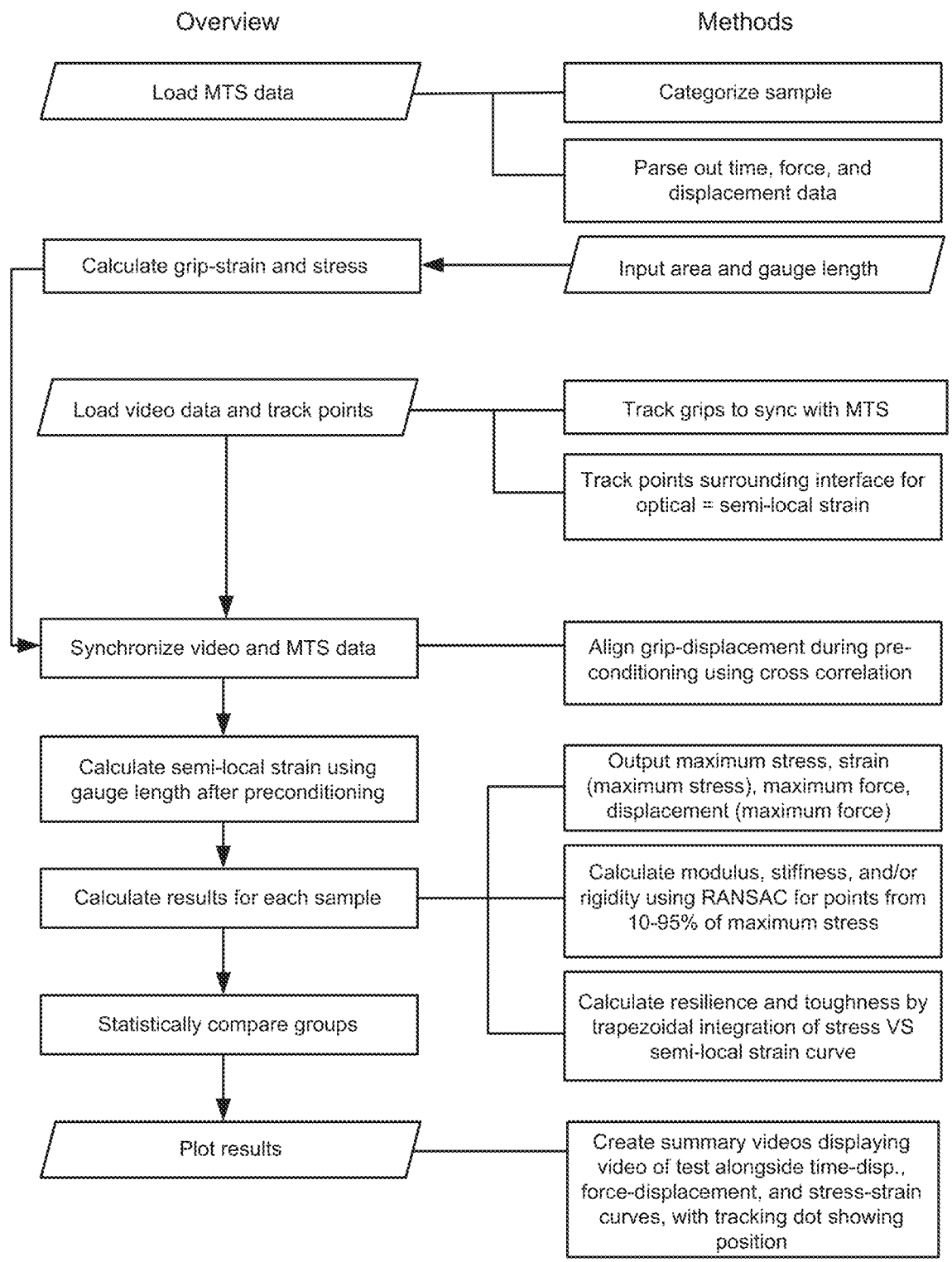
FIG. 15 is a biomechanical analysis flowchart, describing how a custom MATLAB code analyzes mechanical and video data of tendon to bone repairs with adhesive to assess adhesive properties and repair strength improvements.
Figure 16A:
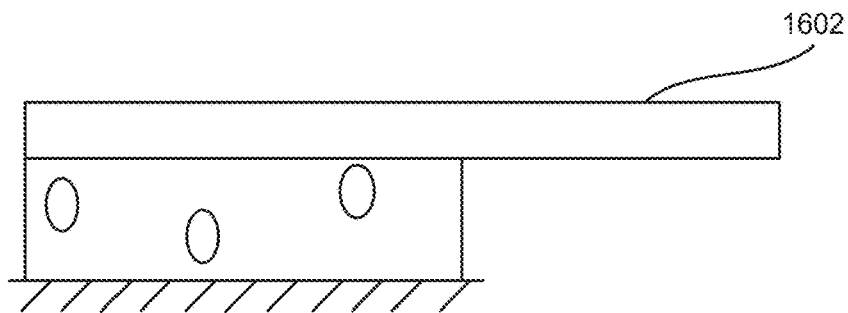
FIG. 16A-FIG. 16D are a series of illustrations showing an envisioned application, in which an adhesive biomaterial film containing soluble factors can release factors locally within the repair site.
Figure 16B:
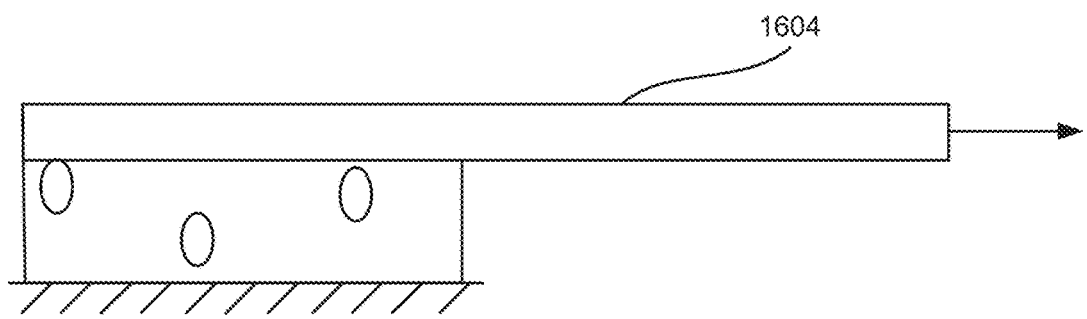
Figure 16C:
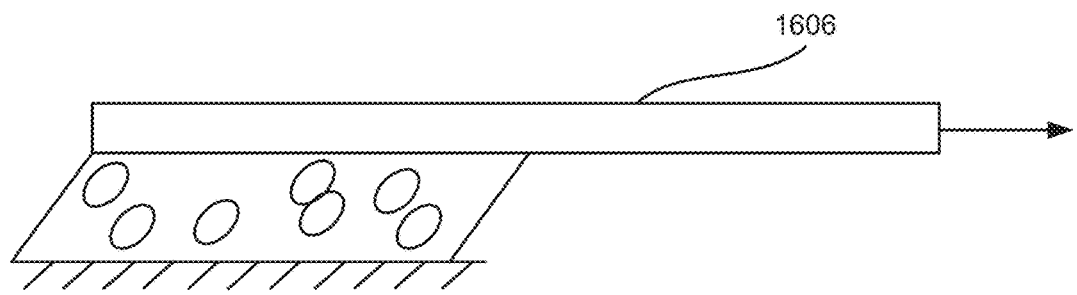
Figure 16D:
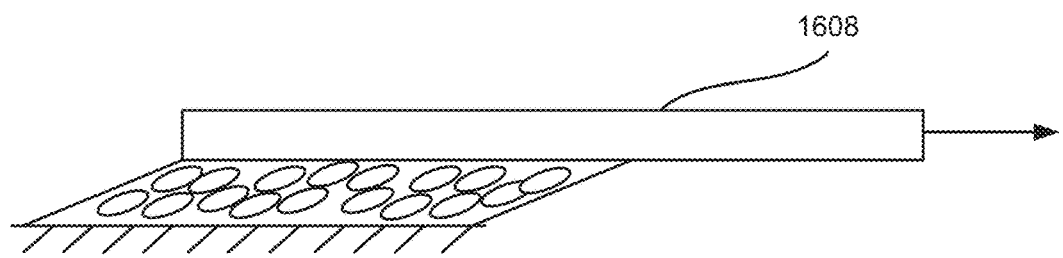
Figure 17:
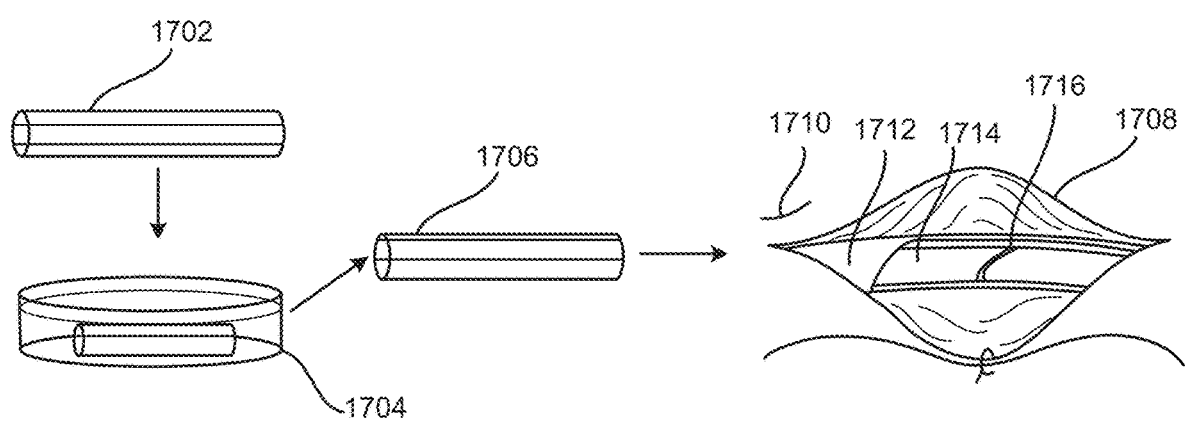
FIG. 17 is a series of schematics showing one envisioned application, where a porous suture could be loaded with an adhesive and applied to a tendon or other connective tissue repair, using a flexor digitorum profundus tendon as an illustrative example.

Biomechanical Analysis:

Fully automated biomechanics analysis was performed using a custom MALAB code following the algorithm given in the flow chart in FIG. 15. Modulus, stiffness, and rigidity were calculated by using random sample correlation (RANSAC) based on Ke Yan's 2011 implementation to quickly find the best fitting line of sufficient bin width. Data is first trimmed to remove data before 10% of max stress and after 95% of max stress to isolate the rough region of interest. Briefly, two points are selected at random and a line is drawn between them, for n=1000 iterations. All data points within a threshold range of 0.5% of the robust fit stress at the 80th percentile are counted as within an acceptable range of the best fit line. Of the n iterations, the iteration with the most inliers is deemed the best fit. This approach is a "robust" fit, which minimizes the effect of outlier points on the best fit line compared to a least squared errors fit. This is confirmed by visual inspection. The "yield" point is determined as the point where the smoothed data first deviates from the RANSAC fit line by 0.1% of the expected stress.

Statistical analysis for all experiments was performed by non-parametric Wilcoxon rank-sum using MATLAB. Statistical significance was set at p<0:05 unless otherwise noted.

Idealized Plank Test Results

Multipartite Adhesive System Tests:

Biomechanical tests of idealized tendon-to-bone planks in lap shear using multipartite adhesives (comprised of 1/16" tendon plank interlayers with Loctite 4903 at interfaces) matched model predictions of maximum load (FIG. 12-FIG. 13). To evaluate a range of adhesive stiffnesses, the 1/16" tendon plank interlayers were first treated with 0 mM, 20 mM, or 100 mM THPC for 15 minutes. Elastic modulus of bovine flexor tendon planks, tested in tension, increased with THPC treatment concentration by 76% for 20 mM THPC and 112% for 100 mM THPC, as expected (n=4 per group, FIG. 13A). When applied in idealized lap shear tests, multipartite adhesive interlayers treated with 0 mM, 20 mM, and 100 mM THPC yielded maximum average shear stresses ($\tau_{ave}$=P/wL) of 324 kPa (±61 kPa standard deviation, n=5), 433 kPa (±132 kPa, n=6), and 494 kPa (±90 kPa, n=5, p=0:008), respectively, (FIG. 13C). This represented a 52% higher failure shear stress and 88% higher yield shear stress (p=0:064, FIG. 13D) with strengthened adhesive bulk interlayers crosslinked with 100 mM THPC, as predicted by shear lag analysis (FIG. 8A). Failure occurred within the tendon plank in most cases, or within the interlayer in some of the cases without THPC crosslinking.

Proof-of-concept experiments demonstrated substantial improvements in load transfer for multipartite cyanoacrylate adhesives in idealized tendon-to-bone plank tests, and for human cadaver rotator cuff repairs (see Example 4). Off-the-shelf cyanoacrylate adhesives (Loctite 4903) are far more stiff than the ideal predicted by the shear lag model. Therefore, a multipartite adhesive comprised of an interlayer (1/16" plank of bovine flexor tendon) adhered to tendon and bone using Loctite 4903 was used to assess a more relevant adhesive shear modulus range. The 324 kPa±61 kPa failure shear stress found experimentally in idealized plank tests (FIG. 13C), equating to a 84.3 N±15.8 N failure load over a 2.6 cm² supraspinatus insertion footprint, closely matched the predicted maximum load from the shear lag model (FIG. 8A, yellow circle). Furthermore, when the tendon plank interlayer was stiffened and strengthened by crosslinking with 100 mM THPC for 15 minutes, the experimental results (494 kPa±90 kPa, equating to 128.5 N±23.4 N) again closely matched the theoretical predictions. Thus, based on idealized plank tests, even the fairly stiff, off-the-shelf cyanoacrylate-based adhesives carry enough load to improve repair strength by approximately 25-40% over a 2.6 cm² supraspinatus repair footprint, when used in conjunction with current repair techniques. That 25-40% increase in load tolerance could substantially decrease repair rupture risk during activities of daily living, thereby facilitating improved healing.

Catechol-Derived Adhesives:

After validating the shear lag model in idealized and clinically-relevant (see Example 4) ex vivo experimental scenarios with various stiffnesses of multipartite adhesives, novel adhesives with the potential for clinical applications were explored. A series of idealized tendon-to-tendon plank lap shear tests was performed using catechol-derived adhesive polymers binding in a hydrated environment (PBS) to assess the adhesive's capacity for arthroscopic use. While homopolymer samples (no crosslinker) and heteropolymer samples (containing crosslinker) that were evaluated without oxidation did not carry meaningful load (0.0-1.5 N), heteropolymer samples that were allowed to oxidize by remaining at 37° C. for 72 hours had several fold higher failure load (4, 6, 18 N), approaching levels that would be clinically meaningful.

Example 4: Human Cadaver Rotator Cuff Repairs

Experimental Methods Section

Surgical Repairs with and without Adhesive:

To assess the potential for adhesive application in a clinically relevant rotator cuff repair setting, paired human cadaver rotator cuff samples were dissected. Human cadaver shoulders were obtained from Anatomy Gifts Registry (Anatomic Gift Foundation, Inc., Hanover, Md.). Supraspinatus tendons were dissected away from the humeral head to ensure full detachment, then tendons were repaired with an open, double row suture anchor surgical repair, in a paired fashion either with or without the multipartite adhesive system described above (Loctite 4903 with a 1/16" thick bovine flexortendon plank compliant interlayer; n=2 per group). Repairs were performed by Dr. William Levine, an experienced shoulder surgeon at Columbia University. To assess the strength of the multipartite adhesive system without suture, the infraspinatus tendons from the same cadaver samples were dissected away from the humeral head, then adhered the tendons to their insertion sites using the same adhesive system before mechanically testing to failure. Tissue was kept hydrated using PBS-soaked gauze throughout this process, once it was dissected. After repair, the humerus and rotator cuff tendons and muscles were carefully dissected from the scapula and surrounding tissue and stored at 4° C. overnight before biomechanical testing the following day. Experiments with 6 shoulders: ~20% improvement in strength.

Biomechanical Testing:

Human cadaver rotator cuff repairs were tested with anMTS 858 Bionix (MTS Eden Prairie, Minn., USA) testing system at Columbia University's Carroll Laboratory, similar to previous methods. Briefly, dissected samples were returned to room temperature and secured in black pipe with two orthogonal bolts and Rockite cement. The insertion site was speckle-coated with VerHoeff stain to facilitate optical tracking. The rotator cuff muscle being tested was secured in a frozen clamp using liquid $CO_2$. The humerus was angled so the muscle was being pulled in line with the direction of the tendon fibers at the insertion. Supraspinatus samples (repaired with double-row suture±adhesive) were first preconditioned with 10 haversine cycles from 1-25 N at 0.5 Hz, followed by a ramp to 10 N at 1 N/s and then a hold at constant load for 5 seconds. Infraspinatus samples (repaired with adhesive only) were preconditioned with 10 haversine cycles from 1-5 N at 0.5 Hz, followed by a ramp to 2.5 N at 1 N/s and then a hold at constant load for 5 seconds. After this preconditioning regimen, samples were pulled in uniaxial tension to failure at 0.5 mm/s with time, force, and MTS grip displacement data measured at a 20 Hz sampling rate. Video was simultaneously recorded from front and side views at 30 Hz. Optical tracking of points on the tendon and bone immediately surrounding the interface enabled accurate determination of semi-local tissue strain, as with idealized plank tests (custom MATLAB code).

Biomechanical Analysis:

Analysis of biomechanical tests was performed as described above in Example 3 (Idealized Ex Vivo Tendon-to-Bone Plank Tests).

Clinically Relevant Cadaver Repair Results

The multipartite adhesive system was further evaluated in human rotator cuff biomechanical tests to test a clinically relevant loading scenario (FIGS. 14A-14D). Cadaver infraspinatus repairs with adhesive only (no sutures) had a maximum shear stress of 115 kPa (±10 kPa, n=4), 35% of the strength of idealized plank tests (FIG. 13). This equated to a maximum load of 34.5 N (±3.0 N), or approximately 10% of the strength of a typical rotator cuff tendon repair.

Figure 14D:
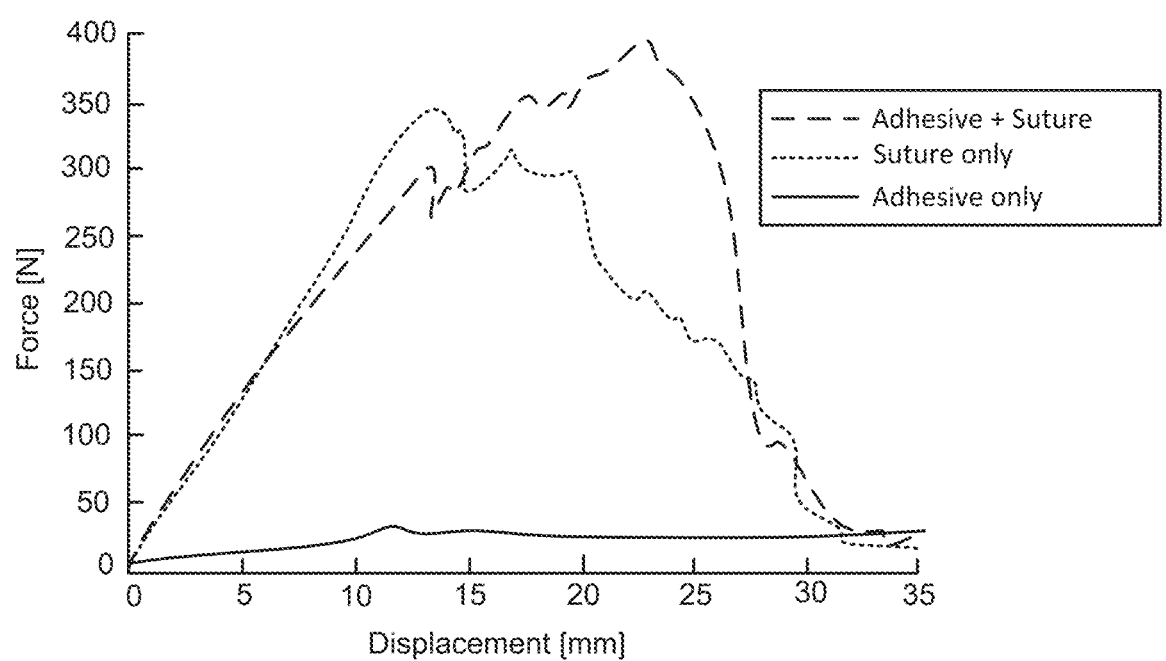
(FIG. 14D) Representative force-displacement curves for biomechanical tests of cadaver supraspinatus repairs with and without adhesive, and for infraspinatus repairs with adhesive only. The adhesive provided an additive improvement in the adhesive and suture repairs compared to the double-row suture only repairs.

Finally, the multipartite adhesive system was assessed in clinical-style human cadaver supraspinatus tenotomy and repair to assess adhesive strength contributions in parallel to a suture repair. Cadaver human supraspinatus tenotomies repaired with double row suture anchor and multipartite adhesive between the supraspinatus tendon and humeral head yielded approximately 40-50 N stronger repairs than paired contralateral control repairs in cases without surgical issues with the suture repair (FIG. 14D). This estimated load improvement is similar to loads carried by infraspinatus tendons adhered without suture, indicating that the adhesive had an additive effect on the strength of the supraspinatus tendon double row bone anchor and suture repair.

In human cadaver rotator cuff experiments using the infraspinatus tendon, the load transferred by the adhesive was 115 kPa±10 kPa (FIG. 13C), equating to 34.5 N±3.0 N, or 35% of the anticipated load from idealized plank tests. It is likely that the human infraspinatus tenotomy and adhesion experiments demonstrated lower strength than the idealized plank tests due to the irregular, curved bony surface and the non-idealized adhesive application and testing conditions. Furthermore, the adhesive only cured for approximately 2 hours in the cadaver experiments, compared to overnight in the idealized plank tests, which may have further limited strength. The cadaver supraspinatus repairs with and without adhesive demonstrated approximate repair strength increases commensurate with the expected additive improvement based on load transferred by adhesive across the infraspinatus tendon insertion (FIG. 14D). This data suggests that the adhesive treatment improved repair strength by approximately 40-50 N, indicating that adhesives provide additive strength improvement over the current suture repairs based on predictions from the infraspinatus adhesive-only experiments.

CONCLUSIONS

Taken as a whole, the multipartite adhesive experiments with and without THPC treatment provide evidence that (i) the shear lag model accurately predicted load transfer across tendon-to-bone for a relevant range of adhesive shear moduli (100 kPa-1 MPa, FIGS. 8A, 13C), and (ii) clinical style repairs demonstrate approximately one-third of the additive load tolerance improvement expected based on the shear lag model and idealized tests. Even this sub-optimal multipartite adhesive material enabled load tolerance increases on the necessary order to improve rotator cuff repair outcomes. Optimal adhesive materials are expected to increase load transfer by approximately 3,000 N compared to current repairs.

The mechanical models and experiments here provide the theoretical underpinnings of a previous study showing that a biological adhesive secreted by the Australian frog Notaden bennetti increased the strength of cadaver sheep infraspinatus repairs by approximately 70-80 N, or 2-fold, over a 16.4±0.2 mm by 13.2±0.1 mm infraspinatus insertion site. Even though this adhesive is neither optimal nor clinically applicable in the current form, this improvement follows the same mechanical principals outlined here: the protein based frog adhesive is elastic ($G_a$=402±7 kPa) with approximately 65% of the adhesive strength of cyanoacrylate and a high shear strength ($\tau_{fail}$=1.7 MPa between wood adherends). The adhesive set in approximately 30-60 seconds and could work while hydrated.

Additional adhesive materials are being developed, including materials within the classes disclosed herein, to fit within the optimal material property ranges predicted by the model, which should yield up to 10-fold higher repair strengths. Such an adhesive would lead to the strength of the tissue itself becoming the limiting factor in the repair. Furthermore, clinically useful adhesives for many tendon-to-bone repair styles need to work in an arthroscopic setting (underwater environment). Therefore, a series of elastomeric polymers with marine mussel-derived, catechol-based binding domains were evaluated. These adhesives were adhered to tissues when fully submerged in PBS to activate catechol binding chemistry and to mimic the arthroscopic environment. As expected, homopolymer adhesives (i.e., no crosslinker to stabilize cohesive strength of the polymer) did not carry clinically relevant loads in the idealized plank tests. Heteropolymer adhesives that were allowed to oxidize and crosslink carried 4-18 N of load. This is on the same order of magnitude as the cyanoacrylate-based multipartite adhesive tests, but with an adhesive that can bind under hydrated conditions. Further studies are needed to assess catechol-derived and other elastomeric bio-adhesives using the simple, standardized lap shear testing protocol described herein to hone adhesive binding and crosslinking chemistries for clinical application.

Strengthening tendon-to-bone insertion repairs is essential to enable adequate healing and functional recovery. Modeling and experimental validation indicate that adhesive films can augment current surgical approaches by transferring stress between tendon and bone over the entire enthesis footprint area, instead of relying only on a small number of anchor points. Even the sub-optimal multipartite adhesives evaluated here for model validation led to load tolerance improvements that are attractive for rotator cuff repair. These and ongoing studies investigating compliant, strong adhesive biomaterials have promise for enhancing rotator cuff repair strength and enabling the requisite tissue apposition for healing.

What is claimed is:

1. A method of repairing a tissue defect at a tissue defect site comprising:
    (i) providing a film or a layer;
    (ii) contacting the film or the layer with an adhesive;
    (iii) delivering the film or the layer to the tissue defect; and (iv) applying the adhesive to the film, the layer, or a tissue, wherein,
the adhesive has a shear modulus ($G_a$) between about $10^3$ and $10^{10}$ Pa;
the adhesive has a failure shear stress value between about $10^5$ Pa and about $10^7$ Pa; or
the adhesive has a strain to failure value between about 3% and about 3000%;
wherein, the film or the layer at the tissue defect site increases post-surgical strength of the tissue defect; increases strength of the tissue defect; reduces post-surgical failure of the tissue defect; improves load transfer of the tissue defect; shifts the load from a few anchor points to shear along the entire film or layer, minimizing stress concentration at the tissue defect site; the tissue defect site comprises a suture and the suture and the film or the layer has an increased strength compared to the tissue defect site with no film or no layer used; or has at least about a 20% increase in strength compared to the tissue defect site with no film or no layer used.

2. The method of claim 1, further comprising:
(i) a suture or an adhesive coated suture;
(ii) a growth factor;
(iii) a cell or cell sheet comprising a cell; or
(iv) a hydrogel or polymer.

3. The method of claim 1, wherein
(i) a hydrogel or a polymer is a delivery agent for the adhesive, a growth factor, or a cell;
(ii) the growth factor is delivered by the hydrogel, a microsphere-based delivery system, or a fibrin-based delivery system;
(iii) the cell is seeded directly onto the film or the layer;
(iv) a suture or an anchor comprises the adhesive;
(v) the adhesive is delivered by the suture;
(vi) the growth factor comprising CTGF/CCN2 is delivered to the tissue defect site;
(vii) the cell is selected from the group consisting of: a living cell, a population of cells, a mesenchymal stromal cell, a tendon-derived stem cell, and an adipose-derived progenitor is delivered to the tissue defect site;
(viii) the hydrogel or the polymer is interspersed with the adhesive, the growth factor, or the cell; or
(ix) the adhesive is structured randomly or tailored to specify or optimize a strength, a toughness, or a stiffness of the adhesive or repair.

4. The method of claim 1, wherein the tissue defect is selected from the group consisting of:
(i) a musculoskeletal injury, a connective tissue-to-bone defect, a connective tissue-to-connective tissue defect, a ligament-to-bone tissue defect, or a tendon-to-bone tissue defect;
(ii) a ligament/tendon-to-bone insertion, an articular cartilage-to-bone junction, a hip labrum, an intervertebral disc, a nucleus pulposus-annulus fibrosus-endplates, a cementumperiodontal ligament-alveolar bone, a muscle-to-tendon, an inhomogeneous or anisotropic tissue, a knee meniscus, a temporomandibular joint disc, a root-periodontium complex, a tendon-bone insertion, a synovial joint, or a fibrocartilaginous tissue; or
(iii) a flexor tendon, a rotator cuff, an anterior cruciate ligament, a meniscus, or an Achilles tendon.

5. The method of claim 1, wherein
(i) the film or the layer is coated with the adhesive;
(ii) the film or the layer comprises one or more selected from the group consisting of a biocompatible film, a polymer nanofiber mesh, an ionic polymer layer, an ionic polymer film, a biodegradable polyester film, a polysaccharide-based film, a polysaccharide-based hydrogel, a polyester film, and a collagen-based matrix, a spacer material, and patterning thereof;
(iii) the adhesive is in contact with the film or the layer;
(iv) the adhesive is applied to the film or the layer, or
(v) the adhesive comprises one or more selected from the group consisting of: a catechol-based adhesive, a DOPA-based adhesive, a mechanically-based adhesive, a fibrin-based adhesive, bioglue, an ionic polymer adhesive, a biodegradable polyester adhesive, a collagen-binding adhesive, and a polysaccharide-based adhesive.

6. The method of claim 1, wherein the shear modulus ($G_a$) between about $10^3$ and $10^{10}$ Pa, the failure shear stress value between about $10^5$ Pa and about $10^7$ Pa, or the strain to failure value between about 3% and about 3000%, identified using a shear lag model or a finite element model, results in reducing elevations of stress in a soft tissue repair.

7. The method of claim 1, wherein the film or the layer is formed from a liquid solution applied to the tissue defect site.

8. A method of surgical repair of a tissue defect at a tissue defect site, the tissue defect comprising a first tissue and a second tissue, comprising:
(i) connecting the first tissue and the second tissue in a subject in need thereof;
(ii) implanting a film or a layer into the subject, wherein the film or the layer is implanted between the first tissue and the film or the layer comprises an adhesive; and
(iii) connecting the first tissue to the second tissue with a suture,
wherein,
the adhesive has a shear modulus ($G_a$) between about $10^3$ and $10^{10}$ Pa;
the adhesive has a failure shear stress value between about $10^5$ Pa and about $10^7$ Pa; or
the adhesive has a strain to failure value between about 3% and about 3000%,
wherein the film or the layer at the tissue defect site increases post-surgical strength of the tissue defect increases strength of the tissue defect; reduces post-surgical failure of the tissue defect; improves load transfer of the tissue defect; shifts the load from a few anchor points to shear along the entire film or layer, minimizing stress concentration at the tissue defect site; the tissue defect site comprising the suture and the film or the layer has an increased strength compared to the tissue defect site with no film or no layer used; or has at least about a 20% increase in strength compared to the tissue defect site with no film or no layer used.

9. The method of claim 8, further comprising:
(i) a growth factor;
(ii) a cell or cell sheet comprising a cell; or
(iii) a hydrogel or polymer.

10. The method of claim 8, wherein
(i) a hydrogel or a polymer is a delivery agent for the adhesive, a growth factor, or a cell;
(ii) the growth factor is delivered by the hydrogel, a microsphere-based delivery system, or a fibrin-based delivery system;

(iii) the cell is seeded directly onto the film or the layer;
(iv) the suture comprises the adhesive;
(v) the adhesive is delivered by the suture and wherein the suture is a porous suture;
(vi) the growth factor comprising CTGF/CCN2 is delivered to the tissue defect site;
(vii) the cell is selected from the group consisting of: a mesenchymal stromal cell, a tendon-derived stem cell, and an adipose-derived progenitor is delivered to the tissue defect site;
(viii) the hydrogel or the polymer is interspersed with the adhesive, the growth factor, or the cell; or
(ix) the adhesive is structured randomly or tailored to specify or optimize a strength, a toughness, or a stiffness of the adhesive or repair.

11. The method of claim 8, wherein the tissue defect is selected from the group consisting of:
(i) a musculoskeletal injury, a connective tissue-to-bone defect, a connective tissue-to-connective tissue defect, a ligament-to-bone tissue defect, or a tendon-to-bone tissue defect;
(ii) a ligament/tendon-to-bone insertion, an articular cartilage-to-bone junction, a hip labrum, an intervertebral disc, a nucleus pulposus-annulus fibrosus-endplates, a cementumperiodontal ligament-alveolar bone, a muscle-to-tendon, an inhomogeneous or anisotropic tissue, a knee meniscus, a temporomandibular joint disc, a root-periodontium complex, a tendon-bone insertion, a synovial joint, or a fibrocartilaginous tissue; or
(iii) a flexor tendon, a rotator cuff, an anterior cruciate ligament, a meniscus, or an Achilles tendon.

12. The method of claim 8, wherein
(i) the film or the layer is coated with the adhesive;
(ii) the film or the layer comprises one or more selected from the group consisting of a biocompatible film, a polymer nanofiber mesh, an ionic polymer layer, an ionic polymer film, a biodegradable polyester film, a polysaccharide-based film, a polysaccharide-based hydrogel, a polyester film, and a collagen-based matrix, a spacer material, and patterning thereof;
(iii) the adhesive is in contact with the film or the layer;
(iv) the adhesive is applied to the film or the layer;
(v) the suture comprises the adhesive; or
(vi) the adhesive comprises one or more selected from the group consisting of: a catechol-based adhesive, a DOPA-based adhesive, a mechanically-based adhesive, a fibrin-based adhesive, bioglue, an ionic polymer adhesive, a biodegradable polyester adhesive, a collagen-binding adhesive, and a polysaccharide-based adhesive.

13. The method of claim 8, wherein the shear modulus ($G_a$) between about $10^3$ and $10^{10}$ Pa, failure shear stress value between about $10^5$ Pa and about $10^7$ Pa, or strain to failure value between about 3% and about 3000%, identified using a shear lag model or finite element model, results in reducing elevations of stress in a soft tissue repair.

14. The method of claim 8, wherein the film or the layer is formed from a liquid solution applied to the tissue defect site.

15. A method of repairing a tissue defect at a tissue defect site comprising:
(i) providing a film or a layer;
(ii) contacting the film or the layer with an adhesive;
(iii) delivering the film or the layer to the tissue defect; and
(iv) applying the adhesive to the film, the layer, or a tissue, wherein,
the adhesive has a shear modulus ($G_a$) between about $10^3$ and $10^{10}$ Pa;
the adhesive has a failure shear stress value between about $10^5$ Pa and about $10^7$ Pa; or
the adhesive has a strain to failure value between about 3% and about 3000%; and
the film or the layer at the tissue defect site increases post-surgical strength of the tissue defect; increases strength of the tissue defect; reduces post-surgical failure of the tissue defect; improves load transfer of the tissue defect; shifts the load from a few anchor points to shear along the entire film or layer, minimizing stress concentration at the tissue defect site; the tissue defect site comprising sutures and the film or the layer has an increased strength compared to the tissue defect site with no film or no layer used; or has at least about a 20% increase in strength compared to the tissue defect site with no film or no layer used.

16. The method of claim 15, further comprising:
(i) a suture or an adhesive coated suture;
(ii) a growth factor;
(iii) a cell or cell sheet comprising a cell; or
(iv) a hydrogel or polymer.

17. The method of claim 15, wherein
(i) a hydrogel or a polymer is a delivery agent for the adhesive, a growth factor, or a cell;
(ii) the growth factor is delivered by the hydrogel, a microsphere-based delivery system, or a fibrin-based delivery system;
(iii) the cell is seeded directly onto the film or the layer;
(iv) a suture or an anchor comprises the adhesive;
(v) the adhesive is delivered by the suture;
(vi) the growth factor comprising CTGF/CCN2 is delivered to the tissue defect site;
(vii) the cell is selected from the group consisting of: a living cell, a population of cells, a mesenchymal stromal cell, a tendon-derived stem cell, and an adipose-derived progenitor is delivered to the tissue defect site;
(viii) the hydrogel or the polymer is interspersed with the adhesive, the growth factor, or the cell; or
(ix) the adhesive is structured randomly or tailored to specify or optimize a strength, a toughness, or a stiffness of the adhesive or repair.

18. The method of claim 15, wherein the tissue defect is selected from the group consisting of:
(i) a musculoskeletal injury, a connective tissue-to-bone defect, a connective tissue-to-connective tissue defect, a ligament-to-bone tissue defect, or a tendon-to-bone tissue defect;
(ii) a ligament/tendon-to-bone insertion, an articular cartilage-to-bone junction, a hip labrum, an intervertebral disc, a nucleus pulposus-annulus fibrosus-endplates, a cementumperiodontal ligament-alveolar bone, a muscle-to-tendon, an inhomogeneous or anisotropic tissue, a knee meniscus, a temporomandibular joint disc, a root-periodontium complex, a tendon-bone insertion, a synovial joint, or a fibrocartilaginous tissue; or
(iii) a flexor tendon, a rotator cuff, an anterior cruciate ligament, a meniscus, or an achilles tendon.

19. The method of claim 15, wherein
(i) the film or the layer is coated with the adhesive;
(ii) the film or the layer comprises one or more selected from the group consisting of a biocompatible film, a polymer nanofiber mesh, an ionic polymer layer, an ionic polymer film, a biodegradable polyester film, a polysaccharide-based film, a polysaccharide-based hydrogel, a polyester film, and a collagen-based matrix, a spacer material, and patterning thereof;

(iii) the adhesive is in contact with the film or layer;

(iv) the adhesive is applied to the film or the layer; or (v) the adhesive comprises one or more selected from the group consisting of: a catechol-based adhesive, a DOPA-based adhesive, a mechanically-based adhesive, a fibrin-based adhesive, bioglue, an ionic polymer adhesive, a biodegradable polyester adhesive, a collagen-binding adhesive, and a polysaccharide-based adhesive.

20. The method of claim 15, wherein the film or the layer is formed from a liquid solution applied to the tissue defect site.

21. A method of surgical repair of a tissue defect at a tissue defect site, the tissue defect comprising a first tissue and a second tissue, comprising:
(i) connecting the first tissue and the second tissue in a subject in need thereof;
(ii) implanting a film or a layer into the subject, wherein the film or the layer is implanted between the first tissue and the film or the layer comprises an adhesive; and
(iii) connecting the first tissue to the second tissue with a suture, wherein,
the adhesive has a shear modulus ($G_a$) between about $10^3$ and $10^{10}$ Pa;
the adhesive has a failure shear stress value between about $10^5$ Pa and about $10^7$ Pa; or
the adhesive has a strain to failure value between about 3% and about 3000%; and
the film or the layer at the tissue defect site increases post-surgical strength of the tissue defect; increases strength of the tissue defect; reduces post-surgical failure of the tissue defect; improves load transfer of the tissue defect; shifts the load from a few anchor points to shear along the entire film or layer, minimizing stress concentration at the tissue defect site; the tissue defect site comprising the suture and the film or the layer has an increased strength compared to the tissue defect site with no film or no layer used; or has at least about a 20% increase in strength compared to the tissue defect site with no film or no layer used.

22. The method of claim 21, further comprising:
(i) a growth factor;
(ii) a cell or cell sheet comprising a cell; or
(iii) a hydrogel or polymer.

23. The method of claim 21, wherein
(i) a hydrogel or a polymer is a delivery agent for the adhesive, a growth factor, or a cell;
(ii) the growth factor is delivered by the hydrogel, a microsphere-based delivery system, or a fibrin-based delivery system;
(iii) the cell is seeded directly onto the film or the layer, (iv) the suture or an anchor comprises the adhesive;
(v) the adhesive is delivered by the suture;
(vi) the growth factor comprising CTGF/CCN2 is delivered to the tissue defect site;
(vii) the cell is selected from the group consisting of: a living cell, a population of cells, a mesenchymal stromal cell, a tendon-derived stem cell, and an adipose-derived progenitor is delivered to the tissue defect site;
(viii) the hydrogel or the polymer is interspersed with the adhesive, the growth factor, or the cell; or
(ix) the adhesive is structured randomly or tailored to specify or optimize a strength, a toughness, or a stiffness of the adhesive or repair.

24. The method of claim 21, wherein the tissue defect is selected from the group consisting of:
(i) a musculoskeletal injury, a connective tissue-to-bone defect, a connective tissue-to-connective tissue defect, a ligament-to-bone tissue defect, or a tendon-to-bone tissue defect;
(ii) a ligament/tendon-to-bone insertion, an articular cartilage-to-bone junction, a hip labrum, an intervertebral disc, a nucleus pulposus-annulus fibrosus-endplates, a cementumperiodontal ligament-alveolar bone, a muscle-to-tendon, an inhomogeneous or anisotropic tissue, a knee meniscus, a temporomandibular joint disc, a root-periodontium complex, a tendon-bone insertion, a synovial joint, or a fibrocartilaginous tissue; or
(iii) a flexor tendon, a rotator cuff, an anterior cruciate ligament, a meniscus, or an achilles tendon.

25. The method of claim 21, wherein
(i) the film or the layer is coated with the adhesive;
(ii) the film or the layer comprises one or more selected from the group consisting of a biocompatible film, a polymer nanofiber mesh, an ionic polymer layer, an ionic polymer film, a biodegradable polyester film, a polysaccharide-based film, a polysaccharide-based hydrogel, a polyester film, and a collagen-based matrix, a spacer material, and patterning thereof;
(iii) the adhesive is in contact with the film or layer;
(iv) the adhesive is applied to the film or the layer; or
(v) the adhesive comprises one or more selected from the group consisting of: a catechol-based adhesive, a DOPA-based adhesive, a mechanically-based adhesive, a fibrin-based adhesive, bioglue, an ionic polymer adhesive, a biodegradable polyester adhesive, a collagen-binding adhesive, and a polysaccharide-based adhesive.

26. The method of claim 21, wherein the film or the layer is formed from a liquid solution applied to the tissue defect site.

\* \* \* \* \*